US009081016B2

(12) United States Patent
Grunert et al.

(10) Patent No.: US 9,081,016 B2
(45) Date of Patent: Jul. 14, 2015

(54) ASSAY FOR MEASUREMENT OF ANTIBODIES BINDING TO A THERAPEUTIC MONOCLONAL ANTIBODY

(71) Applicant: Roche Diagnostics Operations, Inc., Indianapolis, IN (US)

(72) Inventors: Veit Peter Grunert, Munich (DE); Ursula Klause, Indianapolis, IN (US); Pavel Kubalec, Feldafing (DE); Matthias Rothfuss, Penzburg (DE); Barbara Upmeier, Iffeldorf (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 13/766,130

(22) Filed: Feb. 13, 2013

(65) Prior Publication Data

US 2013/0157892 A1 Jun. 20, 2013

Related U.S. Application Data

(63) Continuation of application No. PCT/EP2011/064178, filed on Aug. 17, 2011.

(30) Foreign Application Priority Data

Aug. 19, 2010 (EP) .................... 10173408

(51) Int. Cl.
*C40B 30/04* (2006.01)
*G01N 33/68* (2006.01)

(52) U.S. Cl.
CPC ............ *G01N 33/6854* (2013.01); *C40B 30/04* (2013.01); *G01N 2800/52* (2013.01)

(58) Field of Classification Search
None
See application file for complete search history.

(56) References Cited

U.S. PATENT DOCUMENTS

| 4,062,935 A | 12/1977 | Masson et al. |
| 4,554,088 A | 11/1985 | Whitehead et al. |
| 4,628,037 A | 12/1986 | Chagnon et al. |
| 4,695,393 A | 9/1987 | Whitehead et al. |
| 4,698,302 A | 10/1987 | Whitehead et al. |
| 4,816,567 A | 3/1989 | Cabilly et al. |
| 4,965,392 A | 10/1990 | Fritzberg et al. |
| 5,126,276 A | 6/1992 | Fish et al. |
| 5,219,730 A | 6/1993 | Potocnjak et al. |

(Continued)

FOREIGN PATENT DOCUMENTS

| EP | 0139389 A1 | 5/1985 |
| EP | 0170302 A1 | 2/1986 |

(Continued)

OTHER PUBLICATIONS

International Search Report issued Sep. 23, 2011 in Application No. PCT/EP2011/064178, 3 pages.

(Continued)

*Primary Examiner* — Christian Boesen
(74) *Attorney, Agent, or Firm* — Roche Diagnostics Operations, Inc.

(57) ABSTRACT

Methods and system for determination of an anti-<therapeutic monoclonal antibody> antibody (anti-<TmAB>AB) in vitro in a sample from a patient treated with a therapeutic monoclonal antibody (TmAB). Also, methods and systems for the determination of antigen specific antibodies of a particular immunoglobulin class and for the identification of a patient who is at risk of developing an adverse drug reaction (ADR) during treatment with a TmAB.

9 Claims, 6 Drawing Sheets

(56) References Cited

U.S. PATENT DOCUMENTS

| | | |
|---|---|---|
| 5,432,099 A | 7/1995 | Ekins |
| 5,516,635 A | 5/1996 | Ekins et al. |
| 5,543,112 A | 8/1996 | Ghead et al. |
| 5,545,806 A | 8/1996 | Lonberg et al. |
| 5,545,807 A | 8/1996 | Surani et al. |
| 5,569,825 A | 10/1996 | Lonberg et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,698,449 A | 12/1997 | Baumann et al. |
| 5,750,373 A | 5/1998 | Garrard et al. |
| 5,935,779 A | 8/1999 | Massey et al. |
| 6,316,607 B1 | 11/2001 | Massey et al. |
| 2006/0115907 A1 | 6/2006 | Klause et al. |

FOREIGN PATENT DOCUMENTS

| | | |
|---|---|---|
| EP | 0222146 B1 | 5/1987 |
| EP | 0404097 B1 | 12/1990 |
| EP | 0580979 B1 | 2/1994 |
| EP | 0929319 B1 | 7/1999 |
| EP | 0939319 B1 | 9/1999 |
| EP | 1098198 A1 | 5/2001 |
| EP | 1653233 B1 | 5/2006 |
| WO | 87/02778 A1 | 5/1987 |
| WO | 90/55301 A1 | 5/1990 |
| WO | 90/06515 A1 | 6/1990 |
| WO | 90/11511 A1 | 10/1990 |
| WO | 92/14138 A1 | 8/1992 |
| WO | 93/11161 A1 | 6/1993 |
| WO | 01/36972 A3 | 5/2001 |
| WO | 2005/045058 A3 | 5/2005 |
| WO | 2006/107962 A2 | 10/2006 |
| WO | 2007/109376 A3 | 9/2007 |
| WO | 2008/045976 A3 | 4/2008 |
| WO | 2009/003082 A3 | 12/2008 |

OTHER PUBLICATIONS

Aarden, Lucien et al., "Immunogenicity of anti-tumor necrosis factor antibodies—toward improved methods of anti antibody measurement," Current Opinion in Immunology, 2008, pp. 431-435, vol. 20.

Boerner, Paula et al., "Production of Antigen-Specific Human Monoclonal Antibodies From In Vitro-Primed Human Splenocytes," The Journal of Immunology, Jul. 1991, pp. 86-95, vol. 147, No. 1.

Butler, John E., "Solid Supports in Enzyme-Linked Immunosorbent Assay and Other Solid-Phase Immunoassays," Methods, 2000, pp. 4-23, vol. 22.

Clackson, Tim et al., "Making antibody fragments using phage display libraries," Nature, Aug. 1991, pp. 624-628, vol. 352.

Ekins, R. P. and Chu, F. W., "Multianalyte Microspot Immunoassay—Microanalytical 'Compact Disk' of the Future," Clinical Chemistry, 1991, pp. 1995-1967, vol. 37, No. 11.

Fishwild, Dianne M. et al., "High-avidity human IgGK monoclonal antibodies from a novel strain of minilocus transgenic mice," Nature Biotechnology, Jul. 1996, pp. 845-851, vol. 14.

Galfré, G. and Milstein, C., "[1] Preparation of Monoclonal Antibodies: Strategies and Procedures," Methods in Enzymology, 1981, pp. 3-46, vol. 73.

Groner, Bernd et al., "Therapeutic Antibodies," Current Molecular Medicine, 2004, pp. 539-547, vol. 4.

Harris, Marion, "Monoclonal antibodies as therapeutic agents for cancer," The Lancet Oncology, May 2004, pp. 292-302, vol. 5.

Holliger, Philipp et al., "'Diabodies': Small bivalent and bispecific antibody fragments," Proceedings of the National Academy of Sciences USA, Jul. 1993, pp. 6444-6448, vol. 90.

Hoogenboom, Hennie R. and Winter, Greg, "By-passing Immunisation, Human Antibodies from Synthetic Repertoires of Germline VH Gene Segments Rearranged in Vitro," Journal of Molecular Biology, 1992, pp. 381-388, vol. 227.

Hornauer, Hans et al., "Impact-eine Protein Array Technologie fur die diagnostische Anwendung der Zukunft," BIOspectrum, Special Proteomics, 2004, pp. 564-565, vol. 10.

Hornauer, Hans et al., "Protein Array-Technologie fur die diagnostische Anwendung der Zukunft: IMPACT," Laborwelt, 2004, pp. 38-39, vol. 4.

Jones, Peter T. et al., "Replacing the complementarity-determining regions in a human antibody with those from a mouse," Nature, May 1986, pp. 522-525, vol. 321.

Knight, David M. et al., "The Immunogenicity of the 7E3 Murine Monoclonal Fab Antibody Fragment Variable Region is Dramatically Reduced in Humans by Substitution of Human for Murine Constant Regions," Molecular Immunology, 1995, pp. 1271-1281, vol. 32, No. 16.

Koehler, G. and Milstein, C., "Continuous cultures of fused cells secreting antibody of predefined specificity," Nature, Aug. 1975, pp. 495-497, vol. 256.

Lonberg, Nils et al., "Antigen-specific human antibodies from mice comprising four distinct genetic modifications," Nature, Apr. 1994, pp. 856-859, vol. 368.

Longberg, Nils and Huszar, Dennis, "Human Antibodies from Transgenic Mice," International Reviews of Immunology, 1995, pp. 65-93, vol. 13.

Marks, James D. et al., "By-Passing Immunization: Building High Affinity Human Antibodies by Chain Shuffling," Nature Bio/Technology, Jul. 1992, pp. 779-783, vol. 10.

Marks, James D. et al., "By-Passing Immunization: Human Antibodies from V-gene Libraries Displayed on Phage," Journal of Molecular Biology, 1991, pp. 581-597, vol. 222.

Martin, Charles R. and Mitchell, David T., "Nanomaterials in Analytical Chemistry," Analytical Chemistry News & Features, May 1998, pp. 322A-327A, vol. 70.

Mire-Sluis, Anthony R. et al., "Recommendations for the design and optimization of immunoassays used in the detection of host antibodies against biotechnology products," Journal of Immunological Methods, 2004, pp. 1-16, vol. 289.

Morrison, Sherie, "Success in specification," Nature, Apr. 1994, pp. 812-813, vol. 368.

Morrison, Sherie L. et al., "Chimeric human antibody molecules: Mouse antigen-binding domains with human constant region domains," Proceedings of the National Academy of Sciences USA, Nov. 1984, pp. 6851-6855, vol. 81.

Neuberger, Michael, "Generating high-avidity human Mabs in mice," Nature Biotechnology, Jul. 1996, p. 826, vol. 14.

Pan, Ying et al., "Anti-idiotypic antibodies: biological function and structural studies," FASEB Journal, 1995, pp. 43-49, vol. 9.

Plückthun, A., "Antibodies from *Escherichia coli*," Handbook of Experimental Pharmacology, 1994, Chapter 11, pp. 269-315, vol. 113.

Presta, Leonard G., "Antibody engineering, " Current Opinion in Structural Biology, 1992, pp. 593-596, vol. 2.

Riechmann, Lutz et al., "Reshaping human antibodies for therapy," Nature, Mar. 1988, pp. 323-327, vol. 332.

Sheets, Michael D. et al., "Efficient construction of a large nonimmune phage antibody library: The production of high-affinity human single-chain antibodies to protein antigens," Proceedings of the National Academy of Sciences USA, May 1998, pp. 6157-6162, vol. 95.

Vaughan, Tristan J. et al., "Human Antibodies with Sub-nanomolar Affinities Isolated from a Large Non-immunized Phage Display Library," Nature Biotechnology, Mar. 1996, pp. 309-314, vol. 14.

Wadhwa, W. et al., "Strategies for detection, measurement and characterization of unwanted antibodies induced by therapeutic biologicals," Journal of Immunological Methods, 2003, pp. 1-17, vol. 278.

ASSAY FOR MEASUREMENT OF ANTIBODIES BINDING TO A THERAPEUTIC MONOCLONAL ANTIBODY

CROSS-REFERENCE TO RELATED APPLICATIONS

This application is a continuation of International Application No. PCT/EP2011/064178, filed Aug. 17, 2011 which claims the benefit of European Patent Application No. 10173408.5, filed Aug. 19, 2010, the disclosures of which are hereby incorporated by reference in their entirety.

BACKGROUND OF THE DISCLOSURE

Since the development of the first monoclonal antibodies by Koehler and Milstein in 1974 a lot of effort has been dedicated to the development of antibodies which are appropriate for therapy in humans. The first monoclonal antibodies which became available were developed in mice and rats. In the past ten years an ever growing number of chimeric monoclonal antibodies, humanized monoclonal antibodies or human monoclonal antibodies have reached the market.

Examples of therapeutic monoclonal antibodies ("TmABs") include abciximab (ReoPro®), adalimumab (Humira®), alemtuzumab (Campath®), basiliximab (Simulect®), bevacizumab (Avastin®), cetuximab (Erbitux®), certolizumab pegol (Cimzia®), daclizumab (Zenapax®), eculizumab (Soliris®), efalizumab (Raptiva®), gemtuzumab (Mylotarg®), ibritumomab tiuxetan (Zevalin®), infliximab (Remicade®), muromonab-CD3 (Orthoclone OKT3®), natalizumab (Tysabri®), omalizumab (Xolair®), palivizumab (Synagis®), panitumumab (Vectibix®), ranibizumab (Lucentis®), rituximab (Rituxan®, MabThera®), trastuzumab (Herceptin®) and tositumomab (Bexxar®).

The various kinds of TmAbs available today include chimeric antibodies, e.g. infliximab (an anti-<TNFα>AB), humanized antibodies, e.g. certolizumab (an anti-<TNFα>AB) and human antibodies, e.g. adalimumab (also an anti-<TNFα>AB) or panitumumab (an anti-<epidermal growth factor receptor>AB). Important investigation criteria of humanized or human TmAbs include the induction of auto-antibodies during treatment, adverse drug reactions (ADRs), bio-availability and antibody clearance, for example. Additionally, data relating to the formation of anti-<TmAB>AB is another investigation criteria which may be used for humanized or human TmAbs.

BRIEF SUMMARY OF THE DISCLOSURE

The instant disclosure relates to an immunoassay method for determination of an anti-<therapeutic monoclonal antibody> antibody (anti-<TmAB>AB) in vitro in a sample from a patient treated with a therapeutic monoclonal antibody (TmAB). The method comprises the steps of (a) providing an F(ab) fragment of said TmAB bound to a solid phase, (b) incubating the solid phase provided in (a) with the sample, thereby binding the anti-<TmAB>AB to the solid phase via the F(ab) fragment, (c) incubating the solid phase obtained in (b) with a monoclonal antibody that binds to the anti-<TmAB>AB, (d) detecting the monoclonal antibody bound in (c) and thereby determining the anti-<TmAB>AB in the sample. The disclosure also relates to a method for the determination of antigen specific antibodies of a particular immunoglobulin class by means of an immunoassay in an array format in which the detection of an anti-<TmAB>AB to a TmAB in a sample provided from a patient treated with said TmAB is determined in vitro. Also disclosed is the use of such method for detection of an anti-<TmAB> antibody and for the identification of a patient who is at risk to develop an adverse drug reaction (ADR) during treatment with a TmAB According to embodiments of the instant disclosure, an immunoassay method for determination of an anti-<therapeutic monoclonal antibody> antibody (anti-<TmAB>AB) in vitro in a sample from a patient treated with a therapeutic monoclonal antibody (TmAB), is provided. In some embodiments, the method comprises a) providing an F(ab) fragment of said TmAB bound to a solid phase, b) incubating the solid phase provided in (a) with the sample thereby binding the anti-<TmAB>AB to the solid phase via the F(ab) fragment, c) incubating the solid phase obtained in (b) with a monoclonal antibody <h-Agg.-IgG>, whereby said monoclonal antibody binds to the anti-<TmAB>AB, and d) detecting monoclonal antibody <h-Agg.-IgG> bound in (c) and thereby determining the anti-<TmAB>AB in the sample.

In some embodiments, the present disclosure relates to the use of the immunoassay method for identification of a patient who is at risk to develop an adverse drug reaction (ADR) by determination of an anti-<TmAB>AB in vitro in a sample from a patient treated with a therapeutic monoclonal antibody (TmAB). Some such methods comprise: a) providing an F(ab) fragment of said TmAB bound to a solid phase, b) incubating the solid phase provided in (a) with the sample thereby binding the anti-<TmAB>AB to the solid phase via the F(ab) fragment, c) incubating the solid phase obtained in (b) with a monoclonal antibody <h-Agg.-IgG>, whereby said monoclonal antibody binds to the anti-<TmAB>AB, and d) detecting monoclonal antibody <h-Agg.-IgG> bound in (c) and thereby determining the anti-<TmAB>AB in the sample during treatment with a TmAB, wherein the patient testing positive for anti-<TmAB>AB in the method is at risk of developing an ADR.

In a further embodiments, the present disclosure relates to a method for selecting an alternative therapeutic antibody for a patient under treatment with a first TmAB, wherein at least a first and one or more alternative TmAB are available, comprising: a) determining in vitro an anti-<TmAB>AB to the first TmAB in a sample from a patient treated with said first TmAB, and b) selecting an alternative TmAB for future therapy, if an anti-<TmAB>AB to said first TmAB is present.

According to some embodiments of the present disclosure, a method for determination of an anti-<therapeutic monoclonal antibody> antibody (anti <TmAB> AB) in a sample from a patient treated with a therapeutic monoclonal antibody (TmAB) is provided. In some embodiments, the method comprises the steps of a) providing a F(ab) fragment of the TmAB bound to a solid phase; b) incubating the solid phase with the sample, whereby the anti <TmAB> AB binds to the F(ab) fragment bound to the solid phase; c) incubating the solid phase with a monoclonal antibody <h-Agg.-IgG>, whereby the monoclonal antibody binds to the anti <TmAB> AB bound to the F(ab) fragment; and d) detecting the monoclonal antibody <h-Agg.-IgG> bound in to anti <TmAB>AB bound to the F(ab) fragment bound to the solid phase.

According to some such embodiments, the TmAB is selected from the group consisting of chimeric antibodies (CA) and humanized antibodies (HA). In other embodiments, the TmAB is selected from the group consisting of infliximab, adalimumab, certolizumab and rituximab.

According to further embodiments, the F(ab) fragment is bound to the solid phase by a binding system selected from the group consisting of biotin/steptavidin, biotin/avidin, and biotin/anti-<biotin> antibody. In some embodiments, the monoclonal antibody is an antibody having a dissociation constant ($K_D$) value of between approximately $10^{-6}$ mol/l-$10^{-8}$ mol/l. In some embodiments, the monoclonal antibody <h-Agg.-IgG> is labeled. Exemplary labels in accordance with the embodiments of the instant disclosure provided herein include the detectable label being selected from the group consisting of luminescent labels, chemiluminescent labels, electrochemiluminescent labels, fluorescent labels, and radioactive labels.

In yet another embodiment of the instant disclosure, a method for facilitating a therapeutic decision in a subject is provided. Such method comprises steps of a) obtaining a sample from a subject being treated with a first therapeutic monoclonal antibody (TmAB); b) providing a F(ab) fragment of the first TmAB bound to a solid phase; c) incubating the solid phase with the sample, whereby an anti <first TmAB> AB binds to the F(ab) fragment bound to the solid phase; d) incubating the solid phase with a monoclonal antibody <h-Agg.-IgG>, whereby the monoclonal antibody binds to the anti <first TmAB> AB bound to the F(ab) fragment; e) detecting the monoclonal antibody <h-Agg.-IgG> bound in to anti <first TmAB> AB bound to the F(ab) fragment bound to the solid phase; and f) selecting a second TmAB for future therapy of the subject, if anti <first TmAB> AB to said first TmAB is detected in said step of detecting.

According to some embodiments, the sample is obtained from the subject no later than 14 weeks after first administration of the first TmAB.

Additionally, in yet further embodiments of the present disclosure, a system for facilitating a therapeutic decision in a subject being treated with a therapeutic monoclonal antibody (TmAB) is provided. Some embodiments of the disclosed system include an array having a solid phase and a plurality of test areas spatially separated by inert area of the solid phase, at least one of the plurality of test areas having a F(ab) fragment of the TmAB bound thereto; a binding buffer for facilitating the binding of an anti <therapeutic monoclonal antibody> antibody (anti <TmAB> AB) in a sample from the subject with the F(ab) fragment; a monoclonal antibody <h-Agg.-IgG> having specific binding affinity for the anti <TmAB> AB bound to the F(ab) fragment; a wash buffer for aiding in the removal of monoclinal antibody <h-Agg.-IgG> exposed to the array which is not bound to the anti <TmAB> AB; and a detection means for detection of the monoclinal antibody <h-Agg.-IgG> bound to the anti <TmAB> AB bound to the F(ab) fragment bound to the solid phase of the array.

BRIEF DESCRIPTION OF THE FIGURES

The features of this disclosure, and the manner of attaining them, will become more apparent and the disclosure itself will be better understood by reference to the following description of embodiments of the disclosure taken in conjunction with the accompanying drawing.

Figure 1:
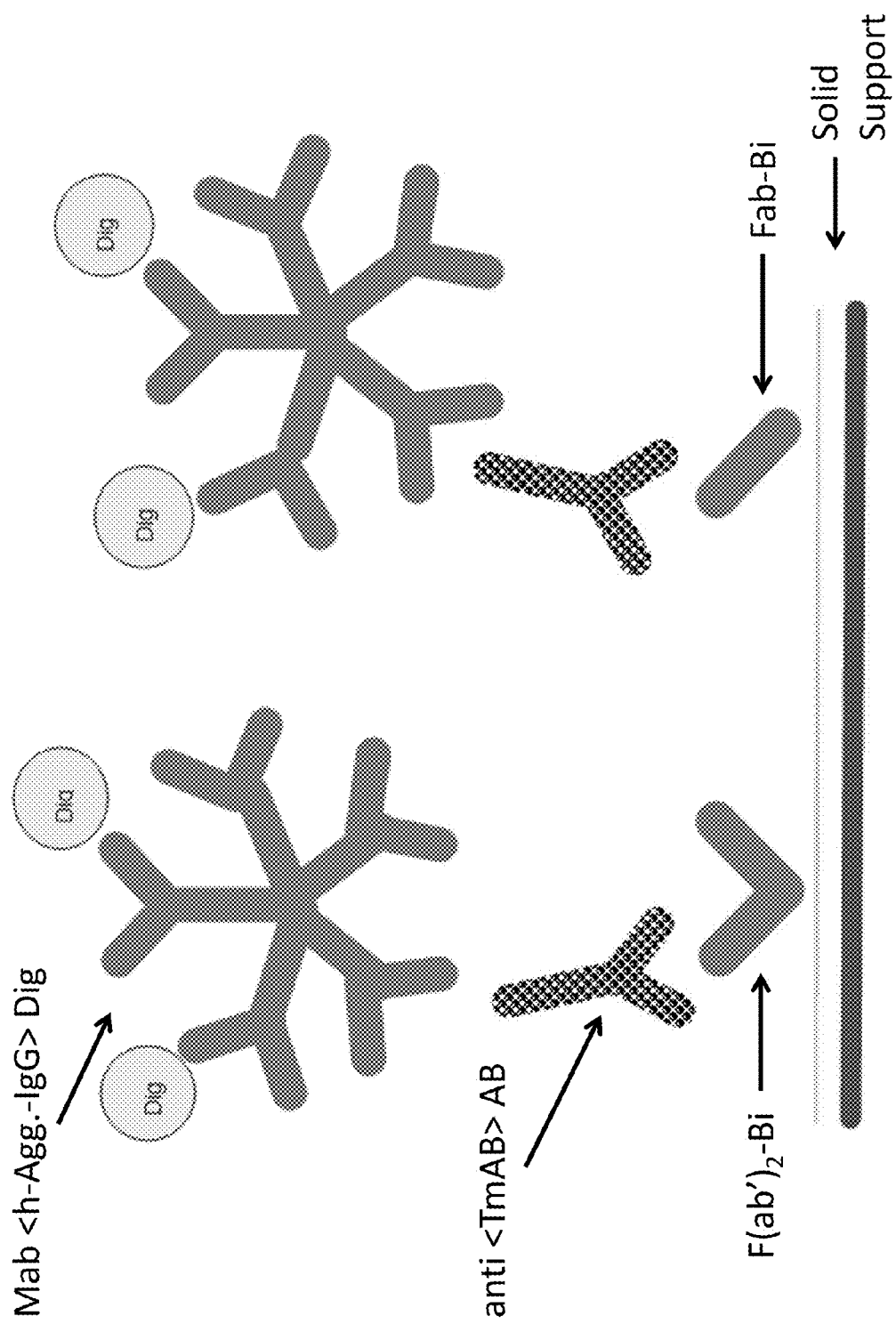
FIG. 1 is a schematic of an indirect immunoassay test format as described in Example 3, depicting an anti-<therapeutic monoclonal antibody> antibody ("anti-<TmAB>AB") being detected in a sample using Dig-labeled monoclonal antibodies ("MAb <h-Agg.-IgG> Dig") with a solid phase having immobilized biotinylated antigens ("F(ab')$_2$-Bi and Fab-Bi") specifically binding anti-<TmAB>AB.

Corresponding reference characters indicate corresponding parts throughout the several views. Although the drawings represent embodiments of the present disclosure, the drawings are not necessarily to scale and certain features may be exaggerated in order to better illustrate and explain the present disclosure. The exemplifications set out herein illustrate an exemplary embodiment of the disclosure, in one form, and such exemplifications are not to be construed as limiting the scope of the disclosure in any manner.

DETAILED DESCRIPTION OF THE DISCLOSURE

The embodiments disclosed herein are not intended to be exhaustive or limit the disclosure to the precise form disclosed in the following detailed description. Rather, the embodiments are chosen and described so that others skilled in the art may utilize their teachings.

The immune system of mammalian organisms produces antibodies which are called immunoglobulins in response to foreign (non-self) substances or infectious agents. Such non-self substances are also referred to as antigens. Mammalian organisms use antibodies to defend itself against the foreign substances or infectious agents.

Immunoglobulins (Ig) can be divided into five different classes, classes M, G, A, E, and D. These five immunoglobulin classes each differ with respect to the composition of the heavy chain, which is referred to as the $\mu$, $\gamma$, $\alpha$, $\epsilon$, or $\delta$ chain.

Each immunoglobulin class has a different function in the organism. Immunoglobulins of the M class occur when a first contact is made with the antigen, the so-called primary immunization. However, the concentration of these immunoglobulins decreases after such first infection. The immunoglobulins of the G class are first formed slowly during a primary immunization and occur in large amounts when there is a second infection with the same antigen. The immunoglobulins of the A class are found on some of the mucosal surfaces of mammalian tissues and are responsible for the defense processes that occur there. The immunoglobulins of the E class are mainly responsible for allergic reactions. The exact function of the immunoglobulins of the D class is up to now unknown.

The individual immunoglobulin classes occur in blood in differing concentrations. Immunoglobulins of the G class (IgG) are the class with the highest occurrence in human serum, being present in a proportion of about 75%, which corresponds to a serum content of approximately 8 to 18 mg/ml. The second most frequent immunoglobulin class is class A (IgA), whose average serum concentration is usually 0.9 to 4.5 mg/ml. Immunoglobulins of the M class (IgM) normally are present at a concentration of 0.6 to 2.8 mg/ml, and immunoglobulins of class D (IgD) are present at a concentration of usually 0.003 to 0.4 mg/ml. IgE antibodies are present in the lowest proportion and only occur at a concentration of about 0.02 to 0.05 µg/ml in serum.

For the differential diagnostics of many diseases, it is important to detect the antibodies of one or more particular class of immunoglobulin. A satisfactory diagnosis in the case of viral, bacterial and parasitic infection can only be ensured by means of a class-specific antibody detection and/or by excluding the interfering measurement of certain other immunoglobulin classes (e.g., detection of IgG and IgA antibodies but no detection of IgM antibodies). This is particularly important for differentiating between fresh or acute infections and older infections as well as to clinically monitor the course of an infection. The class-specific detection of antibodies is especially important for HIV, hepatitis A, hepatitis B, toxoplasmosis, rubella and chlamydia infections. The class-specific detection of antibodies that are specific for a certain antigen is also necessary when determining the titer of protecting antibodies, for example in determining if an immunization has been successful.

Antigen-specific antibodies of a particular class are often detected by binding the antigen-specific antibodies comprised in a sample to a solid phase coated with the specific antigen. The immunoglobulins (Ig) specifically bound to the solid phase via the coated antigen are then detected by detection antibodies that are directed specifically against a certain class of human Ig. However, such a test procedure is only possible when all unspecific, non-antigen-bound Ig is removed by washing before the reaction with the class specific labeled antibodies directed against human Ig. For example, when detecting specific IgG molecules in a sample, relatively large amounts (4-20 mg/ml of serum) of unspecific IgG are present which can bind unspecifically to the solid phase. If a detection antibody against IgG is used, these unspecifically bound immunoglobulins will also be recognized and bound by the detection antibody. This results in elevated background signals and reduced signal-to-noise ratios and last but not least in a reduced sensitivity.

Background signals induced by unspecifically bound immunoglobulins increase the blank value, which makes it more difficult to detect the specifically bound antibodies. This is especially the case for miniaturized test systems such as immunoassays in an array format. Such arrays may comprise a plurality of specific tests, in some cases even in different test formats and the test procedure is performed in a single reaction vessel. Thus, for example, addition of a certain detergent can suppress the unspecific binding of antibodies to a first analyte in such an array, but the same detergent can have no effect or even the opposite effect in another test for detection of a second analyte on the same array system.

A characteristic feature of immunoassays in an array format is the solid phase. In such array-based immunoassays the solid phase preferably consists of localized, defined, discrete test areas. These test areas on the solid phase are preferably spatially separated from one another by inert areas. These localized discrete test areas in most cases are spots and preferably have a diameter of 10 µm to 1 mm and particularly preferably a diameter of 100-200 µm. Array systems are described, for example, in Ekins, R. P. and Chu, F. W. (Clin. Chem. 37 (1995) 1955-1967) and in U.S. Pat. Nos. 5,432,099, 5,516,635 and 5,126,276.

Array systems allow for several analyte determinations to be carried out simultaneously from one sample. The solid phase of these array systems can be preferably coated with a universal binder like streptavidin or avidin as disclosed in EP 0939319 (Hornauer et al.). It is possible to apply a plurality of binding partners such as antigen-specific antibodies to the individual test areas or spots on the solid phase (solid support). In case streptavidin, for example, is used as a universal binding matrix each binding partner can be biotinylated and easily spotted/bound onto such solid phase. Sample components and in particular IgGs can bind unspecifically to one or more of these binding partners or to the solid phase. In this case it is almost impossible to identify a universal buffer additive to reduce the background signals since each individual binding partner might requires a very particular buffer additive. Buffer additives which have positive effects in the case of one binding partner may even have adverse effects for other binding partners. It is also very difficult to modify the solid phase for numerous different binding partners.

As described herein, the present disclosure provides the surprising finding that the use of the immunoassay method disclosed herein for the very early detection of anti-<TmAB>AB and thereby will also allow to identify the majority of those patients at risk to develop an adverse drug reaction (ADR) during treatment with a TmAB The present disclosure employs, in general and unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. 1. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., eds., 1994).

Unless defined otherwise, technical and scientific terms used herein have the same meaning as commonly understood by one of ordinary skill in the art to which this disclosure belongs. Singleton, P. and Sainsburg, D. et al., Dictionary of Microbiology and Molecular Biology $2^{nd}$ ed., J. Wiley & Sons, New York, N.Y. (1994); March, Advanced Organic Chemistry Reactions, Mechanisms and Structure 4th ed., John Wiley & Sons (New York, N.Y. 1992); Lewin, B., Genes V, published by Oxford University Press (1994), ISBN 0-19-854287 9); Kendrew, J. et al. (eds.), The Encyclopedia of Molecular Biology, published by Blackwell Science Ltd. (1994), ISBN 0-632-02182-9); and Meyers, R. A. (ed.), Molecular Biology and Biotechnology: a Comprehensive Desk Reference, published by VCH Publishers, Inc. (1995), ISBN 1-56081-569 8) provide one skilled in the art with a general guide to many of the terms used in the present application.

As used herein, each of the following terms has the meaning associated with it in this section.

The articles "a" and "an" are used herein to refer to one or to more than one (i.e., to at least one) of the grammatical object of the article. By way of example, "an antibody" means one antibody or more than one antibody. The term "at least" is used to indicate that optionally one or more further objects may be present. By way of example, an array comprising at least two discrete areas may optionally comprise two or more discrete test areas.

The expression "one or more" denotes 1 to 50, preferably 1 to 20 also preferred 2, 3, 4, 5, 6, 7, 8, 9, 10, 12, or 15.

The expression "of interest" denotes an analyte or substance of possible relevance that shall be analyzed or determined.

"Detection" includes any means of detecting, including direct and indirect detection. The term "detection" is used in the broadest sense to include both qualitative and quantitative measurements of an analyte, herein measurements of an analyte such as an anti-<therapeutic antibody> antibody. In one aspect, a detection method as described herein is used to identify the mere presence of an analyte of interest in a sample. In another aspect, the method can be used to quantify an amount of analyte in a sample.

By "correlate" or "correlating" it is meant comparing, in any way, the performance and/or results of a first analysis or protocol with the performance and/or results of a second analysis or protocol. For example, one may use the results of a first analysis or protocol in carrying out a second protocols and/or one may use the results of a first analysis or protocol to determine whether a second analysis or protocol should be performed.

To "reduce" or "inhibit" is to decrease or reduce an activity, function, and/or amount as compared to a reference. By reduce or inhibit is meant the ability to cause an overall decrease of 20% or greater, for example, or 50% or greater, and even 75%, 85%, 90%, 95%, or greater. Reduce or inhibit can refer to the symptoms of the disorder being treated.

The biological sample may for example be whole blood, serum, antibodies recovered from the patient or plasma. The sample is preferably whole blood, serum or plasma. The biological sample may comprise antibodies recovered from the patient. In one embodiment, the sample is a clinical sample. In another embodiment, the sample is used in a diagnostic assay.

According to embodiments of the instant disclosure, a sample may be obtained from a subject or patient prior to therapeutic monoclonal antibody (TmAB) therapy. In some embodiments, a sample is obtained from a subject or patient under TmAB therapy. In some embodiments, a sample is obtained from a subject or patient after at least one treatment with a TmAB.

If a sample is stated herein to be taken at week 2, the sample can be taken from the $9^{th}$ day to the $21^{st}$ day after initiation of therapy with said TmAB. If a sample is stated herein to be taken at week 6, the sample can be taken from the $28^{th}$ day to the $64^{th}$ day after initiation of therapy. If a sample is stated herein to be taken at week 14, the sample can be taken from week 13 to week 16 after initiation of therapy.

A "reference sample" as used herein, refers to any sample, standard, or level that is used for comparison purposes. In one embodiment, a reference sample is obtained from an untreated subject or patient. In another embodiment, a reference sample is obtained from a healthy and/or non-diseased individual who is not the subject or patient. In another embodiment, a reference sample is obtained from an untreated individual who is not the subject or patient. In certain embodiments, a reference sample is a single sample or combined multiple samples from the same subject or patient that are obtained at one or more different time points than when the test sample is obtained. For example, a reference sample is obtained at an earlier time point from the same subject or patient than when the test sample is obtained. In certain embodiments, a reference sample includes all types of biological samples as defined above under the term "sample" that is obtained from one or more individuals who is not the subject or patient. In certain embodiments, a reference sample is a combined multiple samples from one or more healthy individuals who are not the subject or patient. In certain embodiments, a reference sample is a combined multiple samples from one or more individuals with a disease or disorder (e.g., rheumatoid arthritis) who are not the subject or patient. In certain embodiments, a reference sample is pooled plasma or serum samples from one or more individuals who are not the subject or patient. In certain embodiments, a reference sample is pooled plasma or serum samples from one or more individuals with a disease or disorder who are not the subject or patient.

The immunoassay method according to the present disclosure is performed in vitro. The patient sample is discarded afterwards. The patient sample is solely used for the in vitro diagnostic method of the disclosure and the material of the patient sample is not transferred back into the patient's body.

According to the instant disclosure, the term "antibody" is used in the broadest sense and specifically covers monoclonal antibodies (including full length monoclonal antibodies), polyclonal antibodies, multispecific antibodies (e.g., bispecific antibodies), and antibody fragments.

The "light chains" of antibodies (immunoglobulins) from many vertebrate species can be assigned to one of two clearly distinct types, called kappa and lambda. This classification and nomenclature is based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3 and IgG4.

The notation of an antibody is written in that the antigen, which is bound specifically by the antibody, is denoted in "<...>", for example, an antibody against the antigen "X" is denoted as an "anti-<X> antibody".

"Antibody fragments" comprise a portion of an intact antibody, preferably comprising the antigen-binding or variable region thereof. Examples of antibody fragments include Fab, Fab', F(ab')$_2$ and Fv fragments; diabodies; linear antibodies; single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')$_2$ fragment that has two antigen-combining sites and is still capable of cross-linking antigen.

The "Fab" fragment contains the variable domains of the antibody light an heavy chains, respectively but also the constant domain of the light chain and the first constant domain (CH1) of the heavy chain.

"Fab'" fragments differ from Fab fragments by having in addition a few amino acid residues at the carboxy terminus of the heavy chain CH1 domain including one or more cysteines from the antibody hinge region. Fab' antibody fragments originally are produced as pairs of Fab' fragments (F(ab')$_2$) which have a hinge cystine bridge between them. The Fab'-monomer is obtained from F(ab')$_2$ by reduction of the cysteine bridge.

"Single-chain Fv" or "scFv" antibody fragments comprise the VH and VL domains of antibody, wherein these domains are present in a single polypeptide chain. Preferably, the Fv polypeptide further comprises a polypeptide linker between the VH and VL domains which enables the scFv to form the desired structure for antigen binding. For a review of scFv, see Plueckthun in The Pharmacology of Monoclonal Antibodies, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404 097; WO 93/11161; and Holliger, P. et al., Proc. Natl. Acad. Sci. USA 90 (1993) 6444-6448.

A "F(ab) fragment" according to the present disclosure, includes Fab, Fab', scFv and diabodies. Fab or Fab' fragments of a TmAB are produced by processing of TmAB, e.g., by digestion of the TmAB into Fab or F(ab')$_2$-fragments and an Fc part, respectively. In case a therapeutic antibody is a scFv or a diabody, these molecules do not need to be further digested but can be used as such in the immunoassay method according to the present disclosure.

The term "monoclonal antibody" (MAb) as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by the hybridoma method first described by Koehler, G. et al., Nature 256 (1975) 495-497, or may be made by recombinant DNA methods (see, e.g., U.S. Pat. No. 4,816,567). The "monoclonal antibodies" may also be isolated from phage antibody libraries using the techniques described in Clackson, T. et al., Nature 352 (1991) 624-628 and Marks, J. D. et al., J. Mol. Biol. 222 (1991) 581-597, for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison, S. L. et al., Proc. Natl. Acad. Sci. USA 81 (1984) 6851-6855).

"Humanized" forms of non-human (e.g., murine) antibodies are chimeric antibodies which contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones, P. T. et al., Nature 321 (1986) 522-525; Riechmann, L. et al., Nature 332 (1988) 323-327; and Presta, L. G., Curr. Op. Struct. Biol. 2 (1992) 593-596.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art. In one embodiment, the human antibody is selected from a phage library, where that phage library expresses human antibodies (Vaughan, T. J. et al., Nature Biotechnology 14 (1996) 309-314; Sheets, M. D. et al., Proc. Natl. Acad. Sci. 95 (1998) 6157-6162; Hoogenboom, H. R. and Winter, G., J. Mol. Biol. 227 (1992) 381-388; Marks, J. D. et al., J. Mol. Biol., 222 (1991) 581). Human antibodies can also be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks, J. D. et al., Bio/Technology 10 (1992) 779-783; Lonberg, N. et al., Nature 368 (1994) 856-859; Morrison, S. L., Nature 368 (1994) 812-813; Fishwild, D. M. et al., Nature Biotechnology 14 (1996) 845-851; Neuberger, M., Nature Biotechnology 14 (1996) 826; Lonberg, N. and Huszar, D., Intern. Rev. Immunol. 13 (1995) 65-93. Alternatively, the human antibody may be prepared via immortalization of human B lymphocytes producing an antibody directed against a target antigen (such B lymphocytes may be recovered from an individual or may have been immunized in vitro). See, e.g., Cole et al., Monoclonal Antibodies and Cancer Therapy, Alan R. Liss, p. 77 (1985); Boerner, P. et al., J. Immunol. 147 (1991) 86-95; and U.S. Pat. No. 5,750,373.

The term "therapeutic antibody" denotes an antibody which is tested in clinical studies for approval as human therapeutic and which can be administered to an individual for the treatment of a disease. In one embodiment the therapeutic antibody is a monoclonal antibody. In a further embodiment the therapeutic antibody is obtained from a great ape or an animal transformed with a human antibody locus or a human monoclonal antibody or a humanized monoclonal antibody. In one embodiment the therapeutic antibody is a human monoclonal antibody. In a further embodiment the therapeutic antibody is a humanized monoclonal antibody. Therapeutic antibodies are being used for the treatment of various diseases such as oncological diseases, immunological diseases, central nervous diseases, vascular diseases, chronic inflammatory diseases, or infectious diseases. Such antibodies are, for instance, antibodies against CD20, CD22, HLA-DR, CD33, CD52, EGFR, G250, GD3, HER2, PSMA, CD56, VEGF, VEGF2, CEA, Levis Y antigen, IL-6 receptor (IL6R), TNFα, or IGF-1 receptor (IGF1R). Therapeutic antibodies are also described by Groner, B., et al., Curr. Mol. Meth. 4 (2004) 539-547; and Harris, M., Lancet Oncol. 5 (2004) 292-302.

As used herein, an "anti-<therapeutic antibody> antibody" is an antibody that binds a therapeutic antibody. An "anti-<therapeutic monoclonal antibody> antibody" (anti-<TmAB>AB) is an antibody that binds a therapeutic monoclonal antibody. For example, an anti-<infliximab>antibody is an antibody that binds infliximab, a therapeutic monoclonal antibody, targeting TNFα.

An antibody that "specifically binds to" or is "specific for" a particular polypeptide or an epitope on a particular polypeptide is one that binds to that particular polypeptide or epitope on a particular polypeptide without substantially binding to any other polypeptide or polypeptide epitope.

An "isolated" polypeptide or "isolated" antibody is one that has been identified and separated and/or recovered from a component of its natural environment. Contaminant components of its natural environment are materials that would interfere with diagnostic or therapeutic uses for the polypeptide or antibody, and may include enzymes, hormones, and other proteinaceous or nonproteinaceous solutes. In preferred embodiments, the polypeptide or antibody will be purified (1) to greater than 95% by weight of polypeptide or antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated polypeptide or antibody includes the polypeptide or antibody in situ within recombinant cells since at least one component of the polypeptide's natural environment will not be present. Ordinarily, however, isolated polypeptide or antibody will be prepared by at least one purification step.

By "subject" or "patient" is meant a mammal, including, but not limited to, a human or non-human mammal, such as a bovine, equine, canine, ovine, or feline, for example.

As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, decreasing the rate of disease progression, amelioration or palliation of the disease state, and remission or improved prognosis. In some embodiments the methods of the disclosure are useful in attempts to delay development of a disease or disorder, especially of an adverse drug reaction.

An "effective amount" refers to an amount effective, at dosages and for periods of time necessary, to achieve the desired therapeutic or prophylactic result. A "therapeutically effective amount" of a therapeutic agent may vary according to factors such as the disease state, age, sex, and weight of the individual, and the ability of the antibody to elicit a desired response in the individual. A therapeutically effective amount is also one in which any toxic or detrimental effects of the therapeutic agent are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The term "diagnosis" is used herein to refer to the identification of a molecular or pathological state, disease or condition or to refer to identification of a patient who may benefit from a particular treatment regimen. The term "prognosis" is used herein to refer to the prediction of the likelihood of clinical benefit from a therapy. The term "prediction" is used herein to refer to the likelihood that a patient will respond either favorably or unfavorably to a particular therapy. In one embodiment, the prediction relates to the extent of those responses. In one embodiment, the prediction relates to whether and/or the probability that a patient will survive or improve following treatment, for example treatment with a particular therapeutic agent, and for a certain period of time without disease recurrence. The predictive methods of the disclosure can be used clinically to make treatment decisions by choosing the most appropriate treatment modalities for any particular patient. The predictive methods of the present disclosure are valuable tools in predicting if a patient is likely to respond favorably to a treatment regimen, such as a given therapeutic regimen, including for example, administration of a given therapeutic agent or combination, surgical intervention, steroid treatment, etc., or whether long-term survival of the patient, following a therapeutic regimen is likely. The term "selecting" and "selection" is used herein to refer to a choice from a number of alternatives. As an example a "selection" is the process to choose one TmAB, from two or more available TmABs available for treatment of a disease.

"Patient response" can be assessed using any endpoint indicating a benefit to the patient, including, without limitation, (1) inhibition, to some extent, of disease progression, including slowing down and complete arrest; (2) reduction in lesion size; (3) inhibition (i.e., reduction, slowing down or complete stopping) of disease cell infiltration into adjacent peripheral organs and/or tissues; (4) inhibition (i.e. reduction, slowing down or complete stopping) of disease spread; (5) relief, to some extent, of one or more symptoms associated with the disorder; (6) increase in the length of disease-free presentation following treatment; and/or (7) decreased mortality at a given point of time following treatment.

"Adverse drug reactions" (ADRs) describe harm associated with the use of given medications at a normal dose. ADRs may be local, i.e. limited to a certain location, or systemic, where a medication has caused ADRs throughout the organism and is e.g. measurable from the circulation. ADRs may be classified by cause (Type A: augmented pharmacologic effects—dose dependent and predictable (intolerance, side effects), Type B: bizarre effects (or idiosyncratic)—dose independent and unpredictable, Type C: chronic effects, Type D: delayed effects, Type E: end-of treatment effects or Type F: failure of therapy), or by severity. The American FDA defines a serious "adverse drug reaction"

(ADR) as one when the patient outcome is one of the following: death, life-threatening, hospitalization (initial or prolonged), disability (significant, persistent, or permanent change, impairment, damage or disruption in the patient's body function/structure, physical activities or quality of life), congenital anomaly, requires intervention to prevent permanent impairment or damage. While no official scale exists yet to communicate overall drug risk, the iGuard Drug Risk Rating System (www.iguard.org) is a five color rating scale: red (high risk), orange (elevated risk), yellow (guarded risk), blue (general risk), Green (low risk). ADRs also comprise infusion reactions. These infusion reactions, e.g. include urticaria, low blood pressure, chest tightness, flushing or decreased blood pressure.

"Lack of efficacy" (LOE) is defined as high disease activity despite treatment with under conditions otherwise considered to be adequate, e.g. with the usually effective amount of a therapeutic agent.

"Treatment Efficacy" is a measure of the ability of an intervention to produce a desired beneficial clinical effect in average conditions of application, usually determined in non-randomized outcome studies. The treatment efficacy could be affected by LOE and/or patients compliance.

The term "benefit" is used in the broadest sense and refers to any desirable effect and specifically includes clinical benefit as defined herein. Clinical benefit can be measured by assessing various endpoints, e.g., inhibition, to some extent, of disease progression, including slowing down and complete arrest; reduction in the number of disease episodes and/or symptoms; reduction in lesion size; inhibition (i.e., reduction, slowing down or complete stopping) of disease cell infiltration into adjacent peripheral organs and/or tissues; inhibition (i.e. reduction, slowing down or complete stopping) of disease spread; decrease of auto-immune response, which may, but does not have to, result in the regression or ablation of the disease lesion; relief, to some extent, of one or more symptoms associated with the disorder; increase in the length of disease-free presentation following treatment, e.g., progression-free survival; increased overall survival; higher response rate; and/or decreased mortality at a given point of time following treatment.

As used herein, the term "Immunoassay" (IA) means a specific binding assay in which an analyte is detected by use of at least one antibody as a specific binding partner or agent. Immunoassay includes, but is not limited to, radioimmunoassay (RIA), fluoroluminescence assay (FLA), chemiluminescence assay (CLA), electrochemiluminescence assay (ECLA), and enzyme linked immunosorbant assay (ELISA). ELISA methods are described, for example, in WO 2001/36972.

The term "detection agent" refers to an agent that binds to an analyte and is detectably labeled. Examples of detection agents include, but are not limited to, an antibody, antibody fragment, soluble receptor, receptor fragment, and the like. Detection of a detection agent is either possible directly, i.e. via a label directly linked to the agent or indirectly via a labeled second binding partner, such as a further antibody or receptor that specifically binds the detection agent.

The term "label" as used herein refers to any substance that is capable of producing a detectable signal, whether visibly or by using suitable instrumentation. Various labels suitable for use in the present disclosure include, but are not limited to, chromogens, fluorescent, chemiluminescent or electrochemiluminescent compounds, catalysts, enzymes, enzymatic substrates, dyes, colloidal metallic and nonmetallic particles, and organic polymer latex particles.

A "directly detectable label" is for example a chromogen (fluorescent or luminescent group and dye), an NMR-active group or a metal particle. Metal chelates which can be detected by electrochemiluminescence are a preferred signal-emitting groups, with particular preference being given to ruthenium chelates, e.g. a ruthenium (bispyridyl)$_3^{2+}$ chelate. Suitable ruthenium labeling groups are described, for example, in EP 0 580 979, WO 90/05301, WO 90/11511 and WO 92/14138.

The term "luminescence" refers to any emission of light that does not derive energy from the temperature of an energy source (for example, a source of electromagnetic radiation, a chemical reaction, mechanical energy). In general, the source causes an electron of an atom to move from a lower energy state into an "excited" higher energy state; then the electron releases that energy in the form of emitted light when it falls back to a lower energy state. Such emission of light usually occurs in the visible or near-visible range of the electromagnetic spectrum. The term "luminescence" includes, but is not limited to, such light emission phenomena such as phosphorescence, fluorescence, bioluminescence, radioluminescence, electroluminescence, electrochemiluminescence and thermo-luminescence.

The term "luminescent label" refers to a label that generates a luminescent signal, e.g. an emission of light that does not derive energy from the temperature of the emitting source. The luminescent label may be, for example, a fluorescent molecule, a phosphorescent molecule, a radioluminescent molecule, a luminescent chelate, a phosphor or phosphor-containing compound, or a quantum dot.

An "electrochemiluminescence assay" or "ECLA" is an electrochemical assay in which bound analyte molecule is detected by a label linked to a detecting agent (target molecule). An electrode electrochemically initiates luminescence of a chemical label linked to a detecting agent. Light emitted by the label is measured by a photodetector and indicates the presence or quantity of bound analyte molecule/target molecule complexes. ECLA methods are described, for example, in U.S. Pat. Nos. 5,543,112; 5,935,779; and 6,316,607. Signal modulation can be maximized for different analyte molecule concentrations for precise and sensitive measurements.

In an ECLA procedure microparticles can be suspended in the sample to efficiently bind to the analyte. For example, the particles can have a diameter of 0.05 µm to 200 µm, 0.1 µm to 100 µm, or 0.5 µm to 10 µm, and a surface component capable of binding an analyte molecule. In one frequently used ECLA-system (Elecsys, Roche Diagnostics, Germany), the microparticles have a diameter of about 3 µm. The microparticles can be formed of crosslinked starch, dextran, cellulose, protein, organic polymers, styrene copolymer such as styrene/butadiene copolymer, acrylonitrile/butadiene/styrene copolymer, vinylacetyl acrylate copolymer, vinyl chloride/acrylate copolymer, inert inorganic particles, chromium dioxide, oxides of iron, silica, silica mixtures, proteinaceous matter, or mixtures thereof, including but not limited to sepharose beads, latex beads, shell-core particles, and the like. The microparticles are preferably monodisperse, and can be magnetic, such as paramagnetic beads. See, for example, U.S. Pat. Nos. 4,628,037; 4,965,392; 4,695,393; 4,698,302; and 4,554,088. Microparticles can be used in an amount ranging from about 1 to 10,000 µg/ml, preferably 5 to 1,000 µg/ml.

A "detection limit" for an analyte molecule in a particular assay is a minimum concentration of the analyte molecule that can be detected above background levels for that assay. For example, in IA and ECLA, the detection limit for an analyte molecule that specifically binds a target molecule can be the concentration at which the analyte molecule produces an IA signal or ECLA signal above that produced by a control antibody that does not bind, or non-specifically binds, the target antigen. Molecules that have an IA response less than the IA detection limit are $IA^-$. Molecules that have an IA response equal to or greater than the IA detection limit are $IA^+$. Molecules that have an ECLA response less than the ECLA detection limit are $ECLA^-$. Molecules that have an ECLA response equal to or greater than the ECLA detection limit are $ECLA^+$. Detection limits can be raised or lowered to achieve a desired assay result.

A "solid phase", also known as "solid support", is insoluble, functionalized, polymeric material to which library members or reagents may be attached or covalently bound (often via a linker) to be immobilized or allowing them to be readily separated (by filtration, centrifugation, washing etc.) from excess reagents, soluble reaction by-products, or solvents. Solid phases for the immunoassays according to the disclosure are widely described in the state of the art (see, e.g., Butler, J. E., Methods 22 (2000) 4-23). The term "solid phase" means a non-fluid substance, and includes particles (including microparticles, beads, magnetic beads, metallic or non-metallic particles) made from materials such as polymer, metal (paramagnetic, ferromagnetic particles), glass, and ceramic; gel substances such as silica, alumina, and polymer gels; capillaries, which may be made of polymer, metal, glass, and/or ceramic; zeolites and other porous substances; membranes; electrodes; microtiter plates; solid strips; and cuvettes, tubes, chips or other spectrometer sample containers. A solid phase component of an assay is distinguished from inert solid surfaces with which the assay may be in contact in that a "solid phase" contains at least one moiety on its surface, which is intended to interact with the capture antibody or capture molecule. A solid phase may be a stationary component, such as a tube, strip, cuvette, chip or microtiter plate, or may be non-stationary components, such as beads and microparticles. Microparticles can also be used as a solid phase for homogeneous assay formats. A variety of microparticles that allow either non-covalent or covalent attachment of proteins and other substances may be used. Such particles include polymer particles such as polystyrene and poly(methylmethacrylate); gold particles such as gold nanoparticles and gold colloids; and ceramic particles such as silica, glass, and metal oxide particles. See for example Martin, C. R., et al., Analytical Chemistry-News & Features 70 (1998) 322A-327A, which is incorporated herein by reference.

The terms "chip", "bio-chip", "polymer-chip" or "protein-chip" are used interchangeably and refer to a collection of a large number of probes, markers or biochemical markers arranged on a shared substrate (e.g. a solid phase) which could be a portion of a silicon wafer, a nylon strip, a plastic strip, or a glass slide.

The term "discrete test area" according to the present disclosure is used to contain a single type of capture molecule. Neighboured discrete test areas on a stationary component solid phase, e.g. an array or a chip, don't overlap each other. In case the solid phase is e.g. an array or a chip, the discrete test areas might be adjacent to each other. Also a spacing in between at least two "discrete test areas" on a stationary component is possible. Discrete test areas on a stationary component solid phase, e.g. on an array or a chip, may be arranged in geometrically patterns. If a solid phase is a non-stationary component, such as beads and microparticles, the term "discrete test area" means that on each non-stationary component one type of capture molecule is immobilized.

An "array", "macroarray" or "microarray" is an intentionally created collection of substances, such as molecules, markers, openings, microcoils, detectors and/or sensors, attached to or fabricated on a substrate or solid surface, such as glass, plastic, silicon chip or other material forming an array. The arrays can be used to measure the levels of large numbers, e.g., tens, thousands or millions, of reactions or combinations simultaneously. An array may also contain a small number of substances, e.g., one, a few or a dozen. The substances in the array can be identical or different from each other. The array can assume a variety of formats, e.g., libraries of soluble molecules, libraries of immobilized molecules, libraries of immobilized antibodies, libraries of compounds tethered to resin beads, silica chips, or other solid phases. The array could either be a macroarray or a microarray, depending on the size of the pads on the array. A macroarray generally contains pad sizes of about 300 microns or larger and can be easily imaged by gel and blot scanners. A microarray would generally contain pad sizes of less than 300 microns.

Methods:

Therapeutic monoclonal antibodies (TmABs) may be used for combating a broad variety of diseases. Application of a TmAB to tumor necrosis factor (<TNFα>) or CD20 (<CD20>), respectively, is of paramount importance for many patients having a diagnosis of a chronic inflammatory disease such as rheumatoid arthritis (RA). These TmABs are also frequently used for treatment of Crohn's disease (CD), ankylosing spondylitis (AS), polyarticular juvenile idiopathic arthritis (JIA), psoriatic arthritis (PsA), Morbus Bechterew or chronic plaque psoriasis (Ps), as well as other diseases. Several TmABs used in therapy of chronic inflammatory disease belong to the group of anti-<TNFα> antibodies.

As discussed in detail above, TmABs are either mouse-human chimeric TmABs (e.g., infliximab) or human TmABs (e.g., adalimumab). TmABs contain elements that might be "foreign" to the immune system of the patient. As such, anti-<TmAB>ABs may occur during treatment with the TmAB as an immune defense reaction of a patient.

When an element of a TmAB is foreign to a patient's immune system, an immune response may be elicited. For example, anti-<TmAB>ABs may be directed against any region of the TmAB such as the variable region, the constant region or the glycostructure of the TmAB. For example, variable domain regions comprising rare sequence elements may cause an immune response by the immune system of a patient treated with a TmAB.

The instant disclosure provides an immunoassay method for the detection of anti-<therapeutic monoclonal antibody> antibodies (anti-<TmAB>ABs) directed against a therapeutic monoclonal antibody (TmAB).

In an embodiment of the present disclosure, an immunoassay method for determination of an anti-<therapeutic monoclonal antibody> antibody (anti-<TmAB>AB) is provided. Such methods comprise an in vitro method, in a sample from a patient treated with a therapeutic monoclonal antibody (TmAB), having the steps of: a) providing a F(ab) fragment of said TmAB bound to a solid phase, b) incubating the solid phase provided in (a) with the sample thereby binding the anti-<TmAB>AB to the solid phase via the F(ab) fragment, c) incubating the solid phase obtained in (b) with a monoclonal antibody <h-Agg.-IgG>, whereby said monoclonal antibody binds to the anti-<TmAB>AB, and d) detecting monoclonal antibody <h-Agg.-IgG> bound in (c) and thereby determining the anti-<TmAB>AB in the sample.

The subject or patient can be any mammalian species. In some embodiments the subject or patient is a human. In such embodiments a human anti-<TmAB>AB is determined in the immunoassay method.

In some embodiments the sample will be selected from the group consisting of a liquid sample like antibodies recovered from the patient, whole blood, plasma, or serum. In a further embodiment the sample will be selected from the group consisting of whole blood, plasma or serum. In some embodiments, the sample is derived from a human.

According to various embodiments of the instant disclosure, the antigen bound to a solid phase for the determination of anti-<TmAB>AB to a TmAB is selected from the group consisting of an Fab' fragment of a TmAB, an Fab fragment of a TmAB, an scFv representing a TmAB and a diabody representing a TmAB. In one preferred embodiment the F(ab) fragment of said TmAB is selected from the group consisting of an Fab' fragment of said TmAB and an Fab fragment of said TmAB. In an exemplary embodiment, the antigen bound to a solid phase for the determination of an anti-<TmAB>AB is a Fab fragment of the TmAB of interest. In some embodiments, the antigen bound to a solid phase for the determination of an anti-<TmAB>AB is a Fab' fragment of the TmAB of interest.

The instant disclosure provides the surprising findings that an immunoassay method, based on the use of an F(ab) fragment of a TmAB of interest bound to a solid phase, can overcome at least some of the current limitations concerning the specificity and sensitivity of the detection of an anti-<TmAB>AB in a sample from a patient treated with said TmAB.

The antigen (e.g., an F(ab) fragment) provided in the immunoassay method in embodiments of the instant disclosure, may be bound to the solid phase by a binding system selected from the group consisting of covalent binding, direct attachment and affinity interaction. A covalent binding of an antigen (e.g. an F(ab) fragment) provided in the immunoassay method can be done for example by an epoxy-, NHS-, carboxymethyl-activation of the solid phase and a subsequent reaction with an appropriate functional group of the antigen. A direct attachment of an antigen (e.g. an F(ab) fragment) provided in the immunoassay method can be based for example on hydrophobic or hydrophilic interactions, chelate binding or adsorptive interactions. An affinity interaction of an antigen (e.g. an F(ab) fragment) can be based for example on biotin/streptavidin-, biotin/avidin-, tag/anti-tag-, lecitin/antibody-, or biotin-anti-<biotin> antibody interactions.

In some embodiments, the antigen provided in immunoassay methods according to the instant disclosure may be bound to the solid phase by a binding system selected from the group consisting of biotin/streptavidin, biotin/avidin, and biotin-anti-<biotin> antibody. To allow such binding the antigen is biotinylated (e.g. F(ab)-Bi fragment). In some embodiments, a F(ab) fragment provided in the method is bound to the solid phase by a binding system selected from the group consisting of biotin/streptavidin and biotin/avidin. In some embodiments, a Fab fragment provided in the method may be bound to the solid phase by a binding system selected from the group consisting of biotin/streptavidin and biotin/avidin. In further embodiments, a Fab' fragment provided in the method may be bound to the solid phase by a binding system selected from the group consisting of biotin/streptavidin and biotin/avidin.

Methods for biotinylation may be used as are known in the art. A detailed description of reaction variants and reaction conditions for conjugating of antibody fragments as well as other proteins and biomolecules is given in G. T. Hermanson: Bioconjugate Techniques, Elsevier/AP, (2008); $2^{nd}$ edition (ISBN: 978-0-12-370501-3), for example. The method for the production of a biotin conjugated Fab fragment (Fab-Bi) of a TmAB according to the present disclosure is described in Example 1.

Attachment of the antigen (e.g. the F(ab) fragment) to the solid phase, according to the instant disclosure, can be accomplished under side controlled conditions so that the antigen binding domain is presented outwards the surface of the solid phase providing the highest accessibility of the antigen using (i) site specific conjugation (e.g., a conjugation in the hinge-region of an F(ab) fragment or a tag-assisted conjugation for example) or (ii) a specific interaction with the solid phase (e.g., a specific sterically oriented interaction of an antigen with a lecitin coated solid phase for example).

In some embodiments of the instant disclosure, the hinge region of a F(ab) fragment is conjugated to the solid phase. In some embodiments, the hinge region of a Fab fragment is conjugated to the solid phase. In some embodiments, the hinge region of a Fab' fragment is conjugated to the solid phase.

In some embodiments of the instant application, a F(ab) fragment is conjugated on the solid phase by a sterically oriented interaction of said F(ab) fragment with a lecitin coated solid phase. According to some embodiments, a Fab fragment is conjugated on the solid phase by a sterically oriented interaction of said Fab fragment with a lecitin coated solid phase. In some embodiments a F(ab) fragment is conjugated on the solid phase by a sterically oriented interaction of said Fab' fragment with a lecitin coated solid phase.

According to some embodiments of the instant disclosure, a stochastic sterically non directed coupling of a F(ab) fragment to the solid phase provides equivalent results as the sterically directed coupling. However, without being bound to this theory, in some circumstances, the directed coupling can be advantageous.

In some embodiments the method according of the present disclosure is practiced with a TmAB of interest selected from the group consisting of chimeric antibodies (CA) and humanized antibodies (HA).

In some embodiments, the method according of the present disclosure is practiced with a biotinylated F(ab) (F(ab)-Bi) fragment of a therapeutic monoclonal antibody (TmAB) selected from the group consisting of abciximab, adalimumab, alemtuzumab, basiliximab, bevacizumab, cetuximab, certolizumab pegol, daclizumab, eculizumab, efalizumab, gemtuzumab, ibritumomab tiuxetan, infliximab, muromonab-CD3, natalizumab, omalizumab, palivizumab, panitumumab, ranibizumab, rituximab, tositumomab and trastuzumab. In an exemplary embodiment, the method is practiced with a F(ab)-Bi fragment of a therapeutic monoclonal antibody (TmAB) selected from the group consisting of infliximab, adalimumab, certolizumab and rituximab. In another exemplary embodiment, is practiced with a F(ab)-Bi fragment of a therapeutic monoclonal antibody (TmAB) selected from the group consisting of infliximab and adalimumab. In another exemplary embodiment, the method is practiced with a F(ab)-Bi fragment of the therapeutic monoclonal antibody (TmAB) infliximab.

In some embodiments the method according of the present disclosure is practiced with a biotinylated Fab (Fab-Bi) fragment of a therapeutic monoclonal antibody (TmAB) selected from the group consisting of abciximab, adalimumab, alemtuzumab, basiliximab, bevacizumab, cetuximab, certolizumab pegol, daclizumab, eculizumab, efalizumab, gemtuzumab, ibritumomab tiuxetan, infliximab, muromonab-CD3, natalizumab, omalizumab, palivizumab, panitumumab, ranibizumab, rituximab, tositumomab and trastuzumab. In an exemplary embodiment, the method according of the present disclosure is practiced with a Fab-Bi fragment of a therapeutic monoclonal antibody (TmAB) selected from the group consisting of infliximab, adalimumab, certolizumab and rituximab. In another exemplary embodiment the method according of the present disclosure is practiced with a Fab-Bi fragment of a therapeutic monoclonal antibody (TmAB) selected from the group consisting of infliximab and adalimumab. In another exemplary embodiment the method according of the present disclosure is practiced with a Fab-Bi fragment of the therapeutic monoclonal antibody (TmAB) infliximab.

According to some embodiments, the method may be practiced with a biotinylated Fab' (Fab'-Bi) fragment of a therapeutic monoclonal antibody (TmAB) selected from the group consisting of abciximab, adalimumab, alemtuzumab, basiliximab, bevacizumab, cetuximab, certolizumab pegol, daclizumab, eculizumab, efalizumab, gemtuzumab, ibritumomab tiuxetan, infliximab, muromonab-CD3, natalizumab, omalizumab, palivizumab, panitumumab, ranibizumab, rituximab, tositumomab and trastuzumab. In an exemplary embodiment the method is practiced with a Fab'-Bi fragment of a therapeutic monoclonal antibody (TmAB) selected from the group consisting of infliximab, adalimumab, certolizumab and rituximab. In another exemplary embodiment the method is practiced with a Fab'-Bi fragment of a therapeutic monoclonal antibody (TmAB) selected from the group consisting of infliximab and adalimumab. In another exemplary embodiment the method is practiced with a Fab'-Bi fragment of the therapeutic monoclonal antibody (TmAB) infliximab.

According to the instant disclosure, and is known in the art, after binding the anti-<TmAB>AB to a solid phase via the F(ab) fragment forming an anti-<TmAB>AB–F(ab) fragment complex, unspecific loosely bound compounds may be removed, for example by a washing step.

According to the instant disclosure, the anti-<TmAB>AB to be determined binds specifically to the F(ab) fragment of the TmAB of interest. In an exemplary embodiment the antibody of interest is an anti-<TNFα> TmAB. In another exemplary embodiment the antibody of interest is selected from the group consisting of infliximab, adalimumab, certolizumab and rituximab. In another exemplary embodiment the antibody of interest is selected from the group consisting of infliximab and adalimumab. In another exemplary embodiment the antibody of interest is infliximab. An "anti-<TmAB>AB–F(ab) fragment complex" is formed, if an anti-<TmAB>AB is present in a sample taken from a patient treated with a TmAB and binds to the F(ab) fragment of said TmAB bound to the solid phase. According to the instant disclosure, the F(ab) fragment of the TmAB and the anti-<TmAB>AB are incubated under conditions allowing for the formation of an anti-<TmAB>AB–F(ab) complex.

According to some embodiments of the instant disclosure, enzyme-linked immunosorbent assay (ELISA) techniques may be used in the investigation of an immunogenic answer of a patient to a TmAB as disclosed herein. In some embodiments, an indirect ELISA format, a sandwich assay ELISA format and a competitive assay ELISA format, double antigen bridging assay (DAGS) or reverse assay. ELISA format are exemplary formats of ELISA techniques which may be used (see, Mire-Sluis, A. R., et al., J. Immunol. Methods 289 (2004) 1-16, summarizing the recommendations for the design and optimization of immunoassays using detection of host antibodies).

In an exemplary embodiment the method according to the present disclosure may be performed in an indirect assay format. As is disclosed herein, surprisingly in the indirect assay format, Fab fragments result in a much better differentiation between negative and truly positive results, as shown in Examples 4 and 5. In examples of such indirect assay format, according to the instant disclosure, a monoclonal antibody <h-Agg.-IgG> is used as detecting monoclonal antibody.

According to some embodiments of the instant disclosure, an immunoassay method may be practiced with a detection antibody <h-Agg.-IgG> having a low affinity for binding the antigen-specific antibodies (anti-<TmAB>ABs). The affinity of an antibody for an epitope is defined as the strength of all non-covalent interactions between the individual antigen-binding site on an antibody and the individual epitope. Antibodies with a low affinity bind weakly and dissociate rapidly whereas high affinity antibodies bind more strongly and remain bound for a longer period of time. The affinity at a binding site does not always reflect the true strength of an antigen-antibody interaction. For example in the case of complex antigens with many repeated antigenic determinants and with complementary antibodies having several low affinity binding sites nonetheless a rather strong binding is observed due to cooperative binding phenomena. The interaction of an antigen and an antigen binding site of an antibody at a first site increases the probability of a reaction at a second antigen binding site of the same antibody. The strength of such multiple interactions between the multivalent antibody and an antigen is referred to as avidity. A high avidity compensates for a low affinity as for example in the case of the pentameric immunoglobulin IgM. In the method according to the disclosure an antibody with a low affinity for the antigen-specific antibody may be used which has several (e.g., at least two, and in some cases at least four and even ten or more) paratopes such as the IgM or IgG immunoglobulins that are cross-linked with one another. Examples of this are rheumatoid factors which are usually composed of IgM molecules and more rarely also of IgG, IgA and IgE molecules.

The value for the affinity of a binding partner, for example an antibody, is determined by the affinity coefficient defined by the model of Langmuir. A molecule with a high dissociation rate constant ($K_{dissoc}$) is likely to have low affinity, as the equilibrium dissociation constant, $K_D=K_{dissoc}/K_{assoc}$. It predicts that the affinity coefficient for a very high binding affinity is about $10^{-9}$ to $10^{-11}$, for a medium binding affinity about $10^{-8}$, for a low binding affinity about $10^{-7}$ and for a very low binding affinity about $10^{-6}$. The detecting monoclonal antibody <h-Agg.-IgG> of the present disclosure possesses a low binding affinity. In an embodiment the detecting monoclonal antibody <h-Agg.-IgG> used in the immunoassay of the present disclosure is an antibody having a $K_D$ value of about $10^{-6}$ mol/l to $10^{-8}$ mol/l. In some exemplary embodiments, the detecting monoclonal antibody <h-Agg.-IgG> is an antibody having a $K_D$ value of about $10^{-7}$ mol/l to $10^{-8}$ mol/l.

As discussed before the determination of the anti-<TmAB>AB in the sample bound in step (c) of the immunoassay method disclosed herein may be performed by a detecting monoclonal antibody <h-Agg.-IgG>. In an exemplary embodiment this detecting monoclonal antibody is of the IgM immunoglobulin class. In some examples, the monoclonal antibody <h-Agg.-IgG> binds antibodies of the immunoglobulin class IgG that have bound to their antigen in a specific manner. This monoclonal antibody only recognizes the densely packed and specifically bound anti-<TmAB>AB, (i.e., those anti-<TmAB>AB that have bound to the F(ab) fragments of the TmABs of interest spotted onto the solid phase). This detection antibody does not react with unspecifically bound or adsorbed IgG.

In some embodiments, the method according to the present disclosure is practiced using a labeled monoclonal antibody <h-Agg.-IgG>. In another exemplary embodiment the monoclonal antibody <h-Agg.-IgG> is labeled with Dig (<h-Agg.-

IgG>-Dig). This Dig-labeled monoclonal antibody <h-Agg.-IgG>-Dig is detected via an anti-<Dig> antibody conjugated to a detectable label. Such detectable label, e.g. can be selected from luminescent labels, chemiluminescent labels, electrochemiluminescent labels, fluorescent labels or radioactive labels.

An exemplary monoclonal antibody <h-Agg.-IgG> used in methods according to the present disclosure is specific for the selected Ig class to be determined. In another embodiment the monoclonal antibody <h-Agg.-IgG> used in the method according to the present disclosure is specific for the IgG class. In an embodiment the monoclonal antibody <h-Agg.-IgG> is capable of detecting all IgG sub-classes.

Surprisingly the instant disclosure demonstrates that the use of a detection monoclonal antibody <h-Agg.-IgG> in an immunoassay method as disclosed in the present disclosure leads to an improved detection of anti-<TmAB>AB in a sample and overcomes at least some of the current limitations in the early detection of anti-<TmAB>AB. Surprisingly the combination of an F(ab) fragment of the TmAB of interest spotted onto the solid phase with the detection antibody <h-Agg.-IgG> in an indirect immunoassay format allows the inventors the very early detection of anti-<TmAB>AB of the IgG class of said TmAB. It is possible to detect anti-<TmAB>AB of the IgG class in vitro in a sample from a patient treated with a TmAB from 2 weeks onwards after first administration of said TmAB. In an exemplary embodiment, the combination of an Fab fragment of the TmAB of interest spotted onto the solid phase with the detection antibody <h-Agg.-IgG> in an indirect immunoassay format allows the detection of anti-<TmAB>AB of the IgG class of said TmAB from 2 weeks onwards after first administration of said TmAB. In another exemplary embodiment the combination of an Fab' fragment of the TmAB of interest spotted onto the solid phase with the detection antibody <h-Agg.-IgG> in an indirect immunoassay format allows the detection of anti-<TmAB>AB of the IgG class of said TmAB from 2 weeks onwards after first administration of said TmAB.

According to some embodiments, the monoclonal antibody <h-Agg.-IgG> used in the method according to the present disclosure is selected from the group consisting of MAb <h-Agg.-IgG>M-3.022.5-IgM (DSM ACC2873), MAb <h-Agg.-IgG>M-1.010.2-IgM and MAb <h-Agg.-IgG>M-1.1.7-IgM (shown in Table 1). In an exemplary embodiment the detecting monoclonal antibody <h-Agg.-IgG> is the MAb <h-Agg.-IgG>M3.022.5-IgM-Dig (DSM ACC2873). In some embodiments, of the instant disclosure including MAb <h-Agg.-IgG>M3.022.5-IgM-Dig demonstrate that immunoglobulins bound unspecifically to the solid phase, i.e. those that are not specifically bound to an antigen, are not recognized or only recognized to a negligible extend. As demonstrated herein, embodiments using MAb <h-Agg.-IgG>M3.022.5-IgM-Dig might substantially reduce the background signal in the immunoassay and thereby keep it at a constant low level independent from possibly interfering IgG comprised in a sample to be analyzed.

Immunoassay methods according to the present disclosure may comprise, in at least one embodiment, being carried out in an array format, e.g. on a chip or bio-chip. In such array format the F(ab) fragment(s) of one or more TmABs are immobilized on discrete areas of the solid phase, which are defined as test areas that are spatially separated from one another. Methods for immobilizing the capture binding partners (e.g. F(ab) fragment(s)) may be accomplished as known in the art, which are for example disclosed in EP 0 929 319 (Hornauer et al.). Additionally, test areas comprising one or more spots containing the same capture binding partner may be present on the solid phase. In an exemplary embodiment, patterns consisting of several identical spots may be formed.

Embodiments of an immunoassay in an array format (e.g. on a chip or bio-chip), according to the instant disclosure, allow for different analytes to be simultaneously determined. In an exemplary embodiment each of the various discrete areas or spots in an array format contains F(ab) fragments of one of the different TmABs of interest, that are able to specifically bind with an anti-<TmAB>AB to be determined. In an exemplary embodiment, such array comprises at least two discrete areas, wherein in each area a different F(ab) fragment of an TmAB of interest (capture molecule) is present. It is also possible to have a combination of F(ab) fragments derived from different TmABs of interest and several spots each containing the F(ab) fragment of one of these different TmABs, respectively, on one array. In an embodiment at least two different F(ab) fragments derived from TmABs of interest each having two or more individual spots are present on such array. In an exemplary embodiment the array used in a method according to the instant disclosure may consist of a support made of metal, glass, a plastic, or polysterene. Polystyrene supports may be used, for example, in the method according to the disclosure which are described, for example, in EP 0939319 (Hornauer et al.). The use of the <h-Agg.-IgG>M3.022.5-IgM-Dig antibody in said method performed in an array format enables that several to a large number of different tests for anti-<TmAB>ABs of interest can be combined on an array. According to embodiments of the instant disclosure, with an array assay format, only one buffer composition is required in each handling step.

Embodiments of the method according to the present disclosure may be performed using a sample provided from a patient prior to 14 weeks after first administration of a TmAB. In some embodiments, a detection of anti-<TmAB>AB performed from 2 weeks onwards after first administration of a TmAB. In some embodiments, a detection of anti-<TmAB>AB is performed at week 2 to 6 after first administration of a TmAB. In other embodiments, a detection of anti-<TmAB>AB is performed at 6 weeks after first administration of a TmAB.

The methods according to the present disclosure are also of a value for the selection of an appropriate TmAB therapy. For example, lack of effectivity (LOE) of a TmAB therapy is a rare but known phenomenon in patients under treatment with a TmAB, e.g. for patients under treatment with an anti-<TNFα> antibody, for example. It is currently unclear what causes, and contributes to the magnitude, of LOE in a patient treated with said TmAB. In some therapeutic approaches the dosage of said TmAB has been raised after a LOE diagnosis or a patient is switched to another TmAB/drug.

Also, the risk of side effects (e.g., such as adverse effects, ADRs) during TmAB therapy, such as anti-<TNFα> therapy, is a known risk. However, there exists no method to assess such risk early after initiation of a TmAB-based therapy, e.g. before severe ADRs set in.

Surprisingly, the instant disclosure provides a method of in vitro determination of antibodies against a TmAB of interest in a sample from a patient under treatment with said TmAB, which allows us to predict which patients are at increased risk to develop an ADR during treatment with a TmAB before an ADR occurs.

In an exemplary embodiment an in vitro determination of antibodies against a TmAB in a sample from a patient under treatment with said TmAB is used to identify patients at risk to develop an ADR during treatment with a TmAB, wherein the patient testing positive for an anti-<TmAB>AB is at risk to develop an ADR. For example, according to the instant disclosure, it may be that in a case where a patient tests positive for anti-<TmAB>ABs against a certain TmAB is then treated with a higher dosage of said TmAB, the risk to develop an ADR thereafter is increased. Therefore, according to the instant disclosure, a change of therapy after determination of anti-<TmAB>AB to the administered first TmAB, to another (second) TmAB may be seriously considered in order to reduce the risk for an ADR later on.

In an exemplary embodiment the method of the current disclosure is used to determine whether a patient is at risk to develop an ADR during treatment with a TmAB. In such embodiments, a patient testing positive for anti-<TmAB>AB is at risk of developing an ADR. A patient testing positive for anti-<TmAB>AB in the method disclosed herein is at increased risk of developing an ADR. Such risk can be determined as a relative risk using mathematical methods known in the art. As shown in the examples provided herein, early development of anti-<TmAB>AB precedes later development of an ADR and/or drop-out of the patients from the study. In an exemplary embodiment, the risk of developing an ADR is a relative risk of at least 40%, and in some embodiments the risk is a relative risk of at least 45%.

Figure 2:
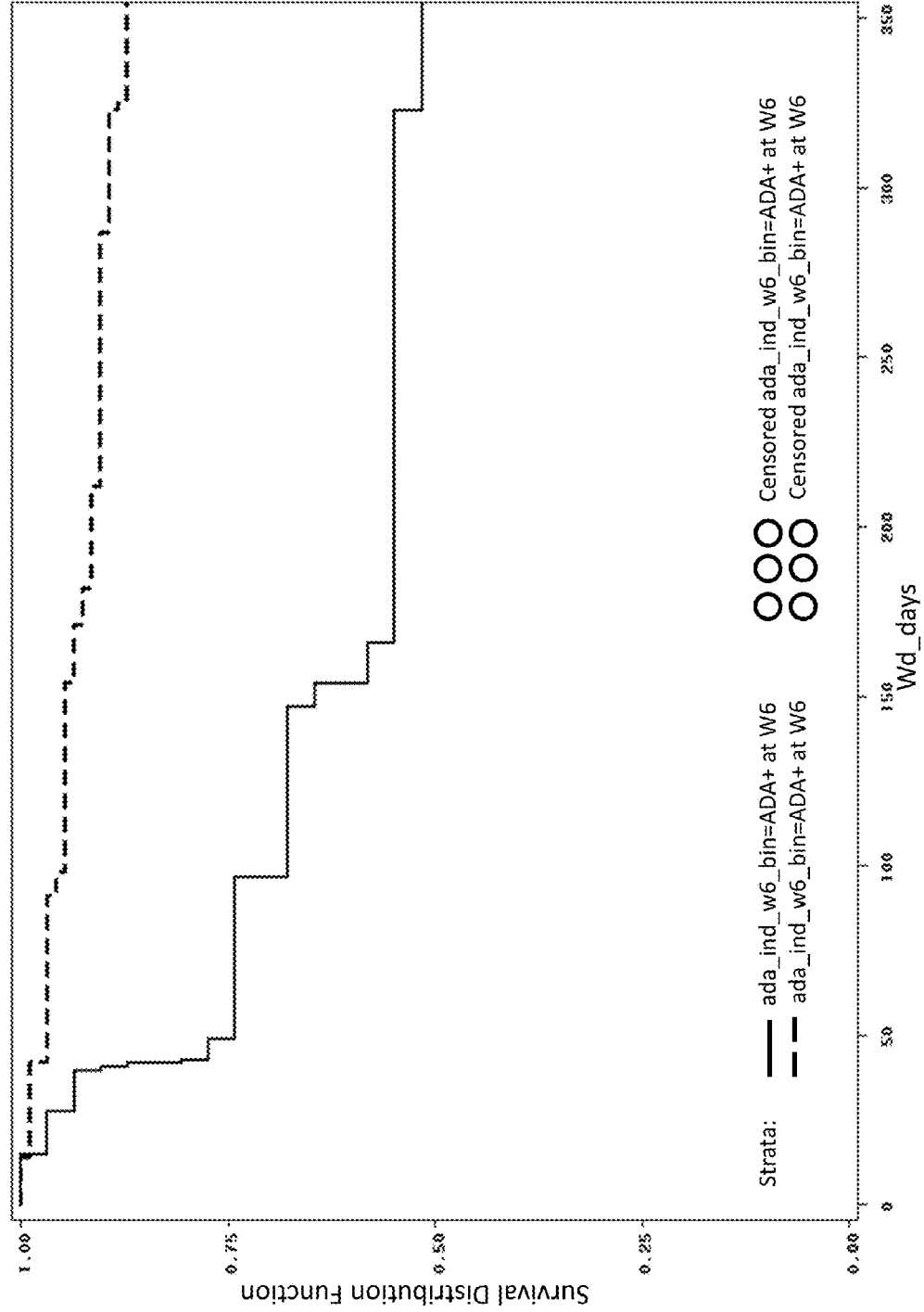
FIG. 2 is a graph showing Kaplan-Meier Survival Curves of patients treated with infliximab which are withdrawl from the study due to ADR at less than or equal to 50 weeks (the X-axis is the day of withdrawl from study, the Y-axis is the survival distribution function, the lower line represents patients with detected anti drug antibodies (anti-<TmAB>AB+) at week 6 (total=31, failed=15) and the upper line represents the patients without detected anti drug antibodies (anti-<TmAB>AB−) at week 6 (total=94, failed=12)). The data has a p-value Log-Rank test of less than 0.0001, a hazard-ratio of 5.06, 95% CI hazard-ratio equal to [2.36, 10.84] (see Table 4).
Figure 3:
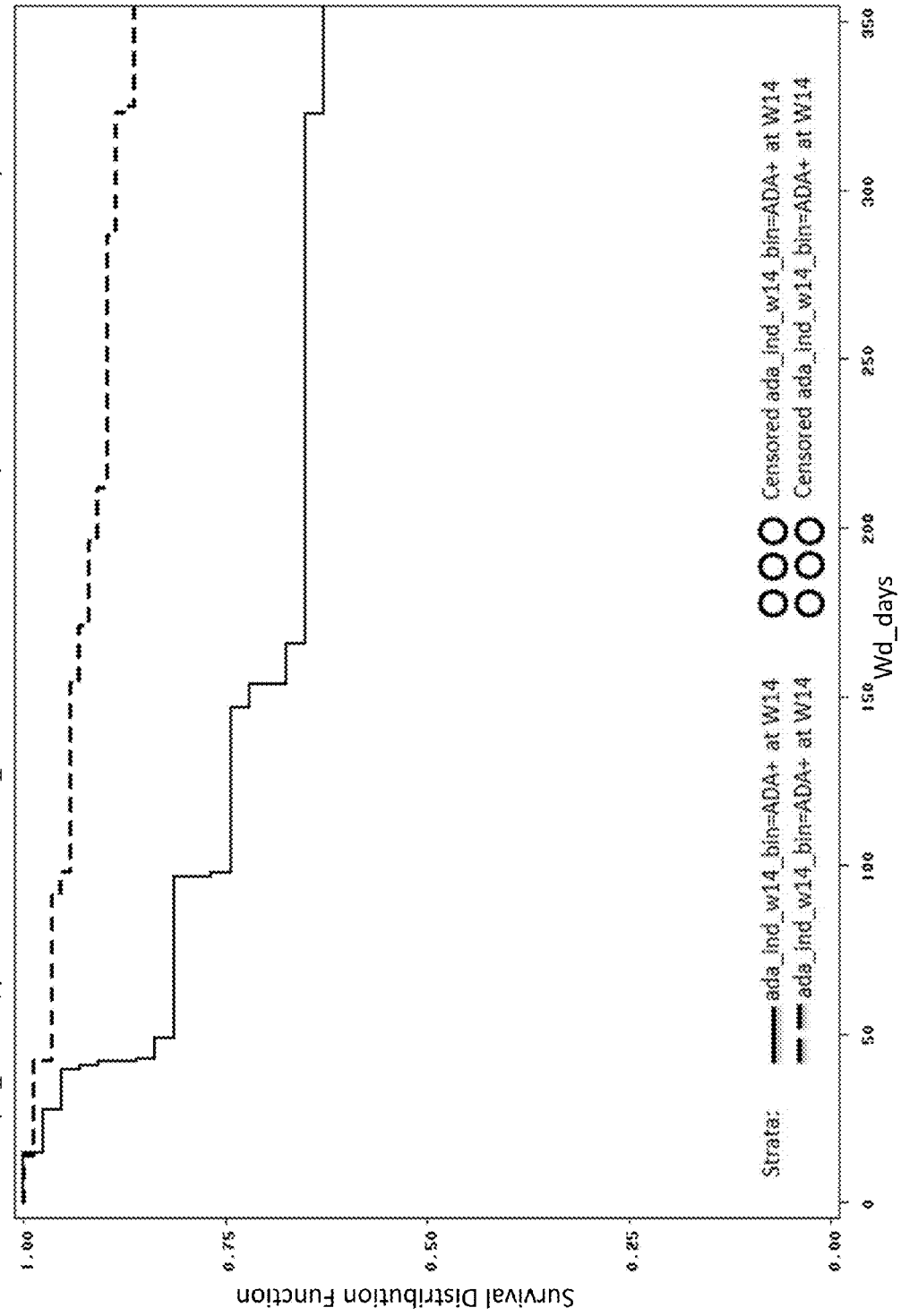
FIG. 3 is a graph showing Kaplan-Meier Survival Curves of patients treated with infliximab which are withdrawl from the study due to ADR at less than or equal to 50 weeks (the X-axis is the day of withdrawl from study, the Y-axis is the survival distribution function, the lower line represents patients with detected anti drug antibodies (anti-<TmAB>AB+) at week 14 (total=43, failed=16), and the upper line represents the patients without detected anti drug antibodies (ADA−) at week 14 (total=88, failed=12)). The data has a p-value Log-Rank test of less than 0.0009, a hazard-ratio of 3.30, 95% CI hazard-ratio equal to [1.56, 6.99] (see Table 4).
Figure 4:
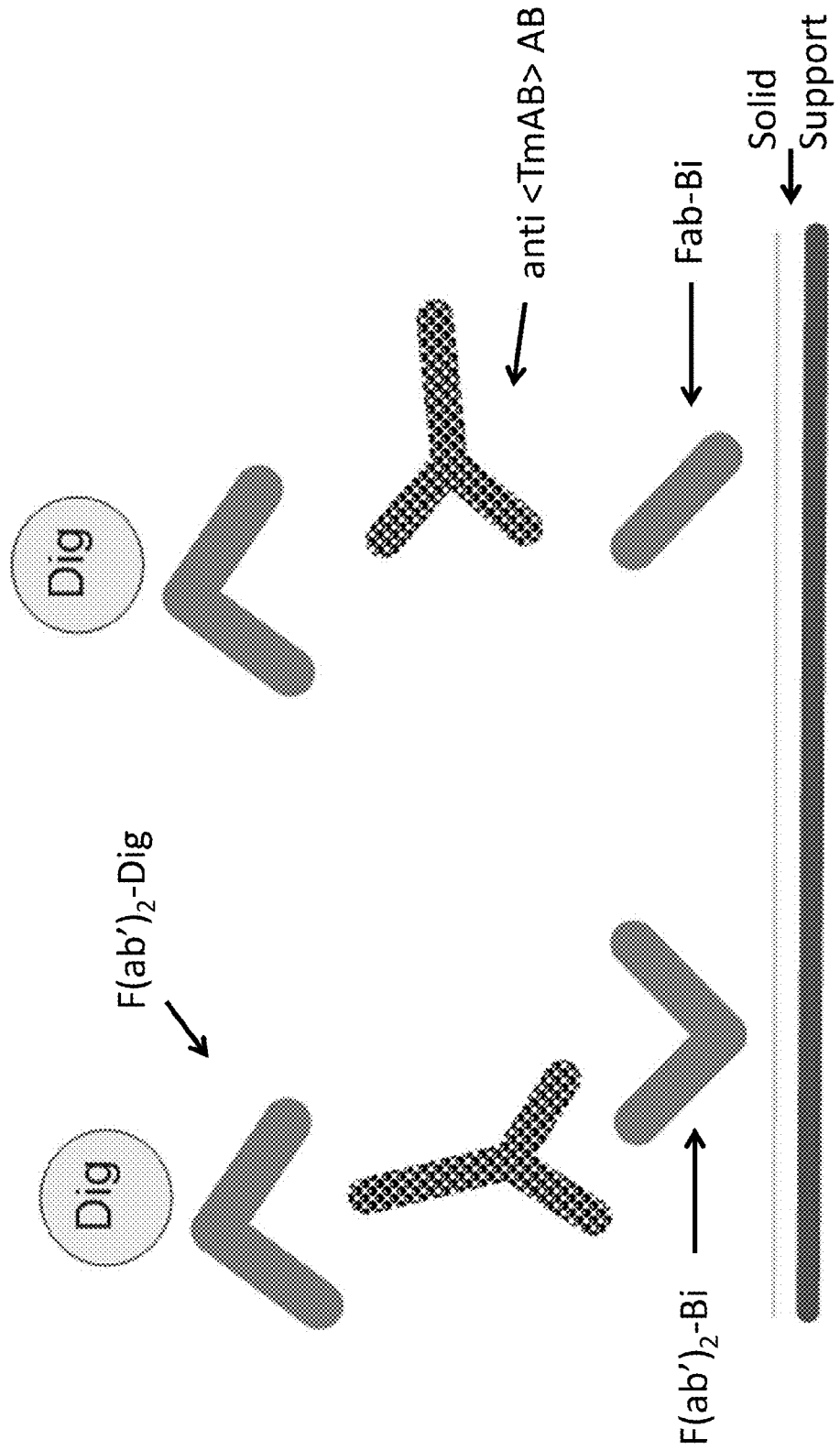
FIG. 4 is a schematic of a sandwich immunoassay, depicting an anti-<TmAB>AB being detected in a sample using Dig-labeled F(ab')$_2$ fragments ("F(ab')$_2$-Dig") with a solid phase having immobilized biotinylated antigens ("F(ab')$_2$-Bi or Fab-Bi") specifically binding anti-<TmAB>AB.

Anti-<TmAB>AB time series plots of FIG. 2 and FIG. 3 show the difference between patients not withdrawn and those withdrawn from study due to an ADR. Study data of Example 5 are represented in FIG. 2, showing the results for patients treated with infliximab as Kaplan-Meier (KM)-curves with respect to anti-<TmAB>AB status at week 6. In FIG. 3 the results for patients treated with infliximab as KM-curves with respect to anti-<TmAB>AB status at week 14 are shown. In both Figures for patients withdrawn due to an ADR (or for patients withdrawn due to no effect of treatment) the KM-curves of anti-<TmAB>AB positive (anti-<TmAB>AB+) patients are lower than the KM-curves of anti-<TmAB>AB negative (anti-<TmAB>AB−) patients. As shown, this difference is even more visible at week 6 than in week 14.

In exemplary embodiments of the present disclosure, methods for selecting an alternative therapeutic antibody for a patient under treatment with a first TmAB are provided, wherein at least a first and one or more alternative TmAB are available, comprising: a) determining in vitro an anti-<TmAB>AB to the first TmAB in a sample from a patient treated with said first TmAB, and b) selecting an alternative TmAB for future therapy, if an anti-<TmAB>AB to said first TmAB is present.

In some embodiments the method for selecting an alternative therapeutic antibody is practiced using a sample obtained from a patient having a diagnosis of a chronic inflammatory disease. In an exemplary embodiment the chronic inflammatory disease is selected from the group consisting of rheumatoid arthritis (RA), Crohn's disease (CD), ankylosing spondylitis (AS), polyarticular juvenile idiopathic arthritis (JIA), psoriatic arthritis (PsA), Morbus Bechterew and or chronic plaque psoriasis (Ps). For example, in an embodiment the patient has a diagnosis of rheumatoid arthritis (RA).

In some embodiments, the method for selecting an alternative therapeutic antibody is practiced using a sample obtained from a human patient. In an embodiment the determined anti-<TmAB>AB is an anti-<TNFαAB>AB.

In some embodiments, of the present disclosure, a method for selecting an alternative TmAB for a patient under treatment with a first TmAB is provided, wherein at least a first and one or more alternative TmAB are available, comprising: a) determining in vitro anti-<TmAB>AB of the IgG class to the first TmAB in a sample from a patient treated with said first TmAB, and b) selecting an alternative TmAB for future therapy, if anti-<TmAB>AB to said first TmAB are present.

In an exemplary embodiment, the method for selecting an alternative therapeutic antibody is performed using a sample provided from a patient no later than 14 weeks after first administration of a TmAB. In another embodiment a detection of anti-<TmAB>AB is performed from 2 weeks onwards after first administration of a TmAB. In some embodiments, a detection of anti-<TmAB>AB is performed at week 2 to 6 after first administration of a TmAB. In an embodiment a detection of anti-<TmAB>AB is performed at 6 weeks after first administration of a TmAB.

According to the instant disclosure, in some embodiments, an alternative TmAB will be selected for future therapy, if an anti-<TmAB>AB to said first TmAB is present in a sample obtained from a patient under treatment of said first TmAB. In an exemplary embodiment the alternative TmAB is selected from the group consisting of an anti-<TNFα> monoclonal antibody and rituximab, for example. In some embodiments, the alternative TmAB may be selected from the group consisting of infliximab, adalimumab, certolizumab and rituximab. In some embodiments the alternative TmAB may be an anti-<TNFα> monoclonal antibody or an anti-<CD20> antibody, or rituximab. In an exemplary embodiment the first TmAB is an anti-<TNFα> monoclonal antibody and the alternative TmAB is an anti-<CD20> antibody, for example. In another embodiment the first TmAB is an anti-<TNFα> monoclonal antibody and the alternative TmAB is rituximab.

Use:

Method according to the present disclosure can generally be used for detection of anti-<TmAB>ABs, both in clinical trial as well as in clinical routine. In an embodiment the present disclosure relates to the use of an immunoassay method of the present disclosure for detection of anti-<TmAB>ABs.

In an exemplary embodiment of the present disclosure, the use of an immunoassay method is disclosed herein for identification of a patient who is at risk to develop an adverse drug reaction (ADR) by determination of an anti-<TmAB>AB in vitro in a sample from a patient treated with a therapeutic monoclonal antibody (TmAB).

In an embodiment, the present disclosure relates to the use of an immunoassay method for determination of an anti-<TmAB>AB in vitro, wherein anti-<TmAB>AB is detected using a sample provided from a patient no later than 14 weeks after first administration of a TmAB. In an embodiment a detection of anti-<TmAB>AB performed from 2 weeks onwards after first administration of a TmAB. In an embodiment a detection of anti-<TmAB>AB is performed at week 2 to 6 after first administration of a TmAB. In an embodiment a detection of anti-<TmAB>AB is performed no later than 6 weeks after first administration of a TmAB.

The method according to the present disclosure can be used to monitor patients treated with a therapeutic monoclonal antibody (TmAB) who are at risk to develop an ADR. The method is used in an embodiment to investigate the frequency of development of anti-<TmAB>AB in patients during treatment with TmAB, and to determine if development of such anti-<TmAB>AB was associated with early ADR and/or treatment failure.

The following examples, illustrative embodiments, and figures are provided for the purpose of demonstrating various embodiments of the instant disclosure and aiding in an understanding of the present disclosure, the true scope of which is set forth in the appended claims. These examples are not intended to, and should not be understood as, limiting the scope or spirit of the instant disclosure in any way. It should also be understood that modifications can be made in the procedures set forth without departing from the spirit of the disclosure.

ILLUSTRATIVE EMBODIMENTS

The following comprises a list of illustrative embodiments according to the instant disclosure which represent various embodiments of the instant disclosure. These illustrative embodiments are not intended to be exhaustive or limit the disclosure to the precise forms disclosed, but rather, these illustrative embodiments are provided to aide in further describing the instant disclosure so that others skilled in the art may utilize their teachings.

1. An immunoassay method for determination of an anti-<therapeutic monoclonal antibody> antibody (anti-<TmAB>AB) in vitro in a sample from a patient treated with a therapeutic monoclonal antibody (TmAB), the method comprising:
   a) providing an F(ab) fragment of said TmAB bound to a solid phase,
   b) incubating the solid phase provided in (a) with the sample thereby binding the anti-<TmAB>AB to the solid phase via the F(ab) fragment,
   c) incubating the solid phase obtained in (b) with a monoclonal antibody <h-Agg.-IgG>, whereby said monoclonal antibody binds to the anti-<TmAB>AB, and
   d) detecting monoclonal antibody <h-Agg.-IgG> bound in (c) and thereby determining the anti-<TmAB>AB in the sample.

2. The method of 1, wherein the sample is whole blood, serum or plasma.

3. The method of 1, wherein the TmAB is selected from the group consisting of chimeric antibodies (CA) and humanized antibodies (HA).

4. The method of 1, wherein the TmAB is selected from the group consisting of infliximab, adalimumab, certolizumab and rituximab.

5. The method of 1, wherein the F(ab) fragment is bound to the solid phase by a binding system selected from the group consisting of biotin/steptavidin, biotin/avidin, and biotin-anti-<biotin> antibody.

6. The method of 1, wherein the monoclonal antibody is an antibody having a dissociation constant (=$K_D$) value of about $10^{-6}$ mol/l-$10^{-8}$ mol/l.

7. The method of 1, wherein the monoclonal antibody <h-Agg.-IgG> is labeled.

8. The method of 1, wherein the monoclonal antibody <h-Agg.-IgG> is labeled with Dig.

9. The method of 8, wherein the Dig-labeled monoclonal antibody <h-Agg.-IgG> is detected by incubating with an anti-<Dig> antibody conjugated to a detectable label.

10. The method of 9, wherein the detectable label is selected from the group consisting of luminescent labels, chemiluminescent labels, electrochemiluminescent labels, fluorescent labels, and radioactive labels.

11. Use of the immunoassay method of 1 for detection of anti-<TmAB> antibodies.

12. Use of a method of 1 for an identification of a patient who is at risk to develop an adverse drug reaction (ADR) during treatment with a TmAB, wherein the patient testing positive for an anti-<TmAB>AB in the method is at risk of developing an ADR.

13. The use according 12, wherein an anti-<TmAB>AB is detected in a sample taken from a patient no later than 14 weeks after first administration of said first TmAB.

14. A method for selecting an alternative therapeutic antibody for a patient under treatment with a first TmAB, wherein at least a first and one or more alternative TmAB are available, comprising:
   a) determining in vitro an anti-<TmAB>AB to the first TmAB in a sample from a patient treated with said first TmAB, and
   b) selecting an alternative TmAB for future therapy, if an anti-<TmAB>AB to said first TmAB is present.

15. The method of 14, wherein the anti-<TmAB>AB can be determined in vitro within a sample provided from a patient no later than 14 weeks after first administration of said first TmAB.

16. The method of 14, wherein the alternative TmAB is selected from the group consisting of an anti-<TNFα> monoclonal antibody and rituximab.

17. The method of 14, wherein the alternative TmAB is selected from the group consisting of infliximab, adalimumab, certolizumab and rituximab.

18. The method of 14, wherein the alternative TmAB is an anti-<TNFα> monoclonal antibody.

19. The method of 14, wherein the alternative TmAB is selected from the group consisting of infliximab, adalimumab and certolizumab.

20. The method of 14, wherein the first TmAB is an anti-<TNFα> monoclonal antibody and the alternative TmAB is rituximab.

EXAMPLES

Example 1

Preparation of Biotin Conjugated Fab and F(ab')$_2$ Fragments of the Specific Therapeutic Monoclonal Antibody Fab Fragment:

The full length therapeutic monoclonal antibody of the immunoglobulin class G (IgG) in 100 mM phosphate, 2 mM EDTA buffer, pH 7.0 was incubated with papain in the presence of 10-20 mM cysteine (5 to 20 mU papain per mg IgG). The fragmentation was analyzed by analytical gel permeation chromatography and stopped after 60-120 minutes by addition of iodacetamide solution (ad 10 mM).

F(ab')$_2$ Fragment:

The full length therapeutic antibody of the immunoglobulin class G (IgG) in 100 mM sodium citrate buffer, pH 3.7 was incubated with pepsin (1 to 15 µg pepsin per mg IgG). The fragmentation was analyzed by analytical gel permeation chromatography and stopped after 90 minutes by adjusting the pH value to 6.5 by the addition of potassium phosphate.

Purification:

Both fragmentation mixtures were each dialysed against 10 mM sodium phosphate buffer with 10 mM sodium chloride, pH 5.5, the solution was applied to an SP-sepharose chromatography column, the isolated fractions eluted in a salt gradient were analyzed individually by analytical gel filtration. The pool containing the antibody Fab or F(ab)'$_2$ fragments were applied to an affinity matrix with immobilized polyclonal antibodies against human Fcg to eliminate trace amounts of Fcg fragments, the flow through was pooled and analyzed to a residual Fcg content. The affinity purification procedure was repeated at least three times until the residual Fcg concentration fell below 0.5 ppm. The product was concentrated to about 10 mg/ml and finally applied to a gel filtration column (Superdex 200).

Conjugation:

the purified Fcg-free fragments were conjugated using NHS activated biotin labels at pH value of 8.2 to 8.4. The reaction stoichiometry was 1:5 (IgG:label), the reaction was stopped by addition of 1 M lysine solution after 1 hour and the raw conjugates were purified on a gel filtration column (Superdex 200).

Preparation of Biotin Conjugated Fab Fragment of the Specific Therapeutic Antibody:

The purified F(ab')$_2$ fragment was incubated with 5 mM cysteamine for 1 hour, the reduction to a Fab fragment was monitored by analytical gel permeation chromatography. The raw product was applied to a gel filtration column (Superdex 200) and the pooled Fab fractions were immediately conjugated with MEA activated biotin labels (stoichiometry 1:10, 1 hour). The final analytical characterization was performed by ESI-MS in order to confirm the conjugation site and yield, respectively.

Example 2

Production of Monoclonal Mouse IgM Antibodies with Rheumatoid Factor-Like Specificity Immunogen: H-IgG Polymer:

10 mg human IgG1 (Sigma Company) is dissolved in 0.6 ml 25 mM bicarbonate buffer pH 9.5. After adding 3.5 µl 12.5% glutardialdehyde solution, it is incubated for 2 hours at room temperature. Subsequently it is cooled in an ice bath, adjusted to pH 8.3 with 50 mM triethanolamine solution pH 8.0 and 0.15 ml freshly prepared sodium boron hydride solution (8 mg boron hydride/ml water) is added. After 2.5 hours at 0° C. the preparation is dialysed for 16 hours at 4° C. against 10 mM potassium phosphate buffer/0.2 M NaCl, pH 7.5. The dialysate containing IgG polymer is stored in aliquots at −80° C. or used for immunization and for specificity tests in culture supernatants of hybridoma cells. H-IgG3 polymer is produced in a similar manner starting from human IgG3 (Sigma Company).

Immunization of Mice:

12 week old, female Balb/c mice are firstly immunized intraperitoneally with 100 µg H-IgG1 or IgG3 polymer together with the adjuvant CFA (complete Freund's adjuvant). After 8 days a further immunization is carried out with 100 µg of the respective IgG polymer in CFA. 13 days after the initial immunization, 200 µg of the respective polymer is administered intraperitoneally without adjuvant, 14 and 15 days after the initial immunization 100 µg was administered in each case intraperitoneally and intravenously. The fusion is carried out after 16 days.

Production of Hybridoma Clones:

Fusion and Cloning:

Spleen cells of an immunized mouse are fused with myeloma cells following the method of Galfré, G., Methods in Enzymology 73 (1981) 3-46. Approximately 1×10$^8$ spleen cells of the immunized mouse are mixed with 2×10$^7$ myeloma cells (P3X63-Ag8-653, ATCC CRL 1580) and centrifuged (10 min at 300 g and 4° C.). The cells are then washed once with RPMI-1640 medium without foetal calf serum (FCS) and again centrifuged at 400 g in a 50 ml conical tube. 1 ml PEG (polyethylene glycol) (molecular weight 4000, Merck, Darmstadt) is added and mixed by pipetting. After 1 min in a water bath at 37° C., 5 ml RPMI 1640 without FCS is added dropwise, mixed, filled up to 50 ml with medium (RPMI 1640+10% FCS) and subsequently centrifuged. The sedimented cells are taken up in RPMI 1640 medium containing 10% FCS and sown in hypoxanthine-azaserine selection medium (100 mmol/l hypoxanthine, 1 µg/ml azaserine in RPMI 1640+10% FCS). Interleukin 6 (100 U/ml) is added to the medium as a growth factor. After about 10 days the primary cultures were tested for specific antibody synthesis. Primary cultures which show a positive reaction with aggregated human IgG1 but no cross-reaction with monomeric IgG are cloned by means of a fluorescence-activated cell sorter in 96-well cell culture plates. Interleukin 6 (100 U/ml) is added to the medium as a growth additive.

The following hybridoma clones were obtained in this manner:

TABLE 1

Screening test for monoclonal antibodies having specificity for aggregated, human IgG

| Monoclonal antibody name | Immunogen | Subclass specificity |
|---|---|---|
| MAb < h-Agg.-IgG > M-3.022.5-IgM | h-IgG1 polymer | IgG1 > IgG3 > IgG4 > IgG2 |
| MAb < h-Agg.-IgG > M-1.010.2-IgM | h-IgG1 polymer | IgG1 > IgG3 > IgG4 > IgG2 |
| MAb < h-Agg.-IgG > M-1.1.7-IgM | h-IgG3 polymer | IgG1 > IgG3 > IgG2 > IgG4 |

Streptavidin-coated MTPs are coated with biotinylated human IgG1 or IgG3. Afterwards they are incubated with the monoclonal antibody in the cell culture supernatant. Subsequently the bound antibodies are detected in the usual manner using an anti-<mouse-IgM>-POD by reaction with a POD substrate.

Determination of the subclass specificity using human IgG bound to a solid phase: In order to determine the specificity of the antibodies in the culture supernatant of the hybridoma cells, MTPs coated with recombinant streptavidin (Micro-Coat Company, Order No. 12-K 96 N) are coated with 1 µg/ml biotinylated h-IgG (=h-IgG-Bi) of subclass 1 or 2 or 3 or 4 in incubation buffer. Since IgG bound via biotin to a solid phase behaves like aggregated, polymeric IgG, this experimental approach can be used to determine the subclass specificity. For this 100 µl h-IgG-Bi solution per well is incubated for 60 minutes at room temperature while shaking and subsequently washed 3 times with 0.9% NaCl/0.05% Tween® 20.

In the next step 100 µl of the antibody solution to be examined (culture supernatant) is added to a coated well and incubated for 1 hour at room temperature while shaking. After washing 3 times with 0.9% sodium chloride/0.05% Tween® 20, 100 µl of a POD-labeled Fab fragment of a polyclonal antibody from the goat against mouse IgM (Dianova Company, Order No. 115-036-075, concentration used 0.16 µg/ml incubation buffer) is added in each case to detect bound antibody from the sample, incubated for 1 hour at room temperature while haking and subsequently washed 3 times with 0.9% sodium chloride/0.05% Tween® 20.

Finally 100 µl/well ABTS® substrate (Roche Diagnostics GmbH, Order No. 1684 302) is added and the absorbance at 405/492 nm is measured after 30 min at room temperature in an MR700 Microplate reader from the Dynatech Company.

Incubation Buffer:

40 mM Na phosphate, pH 7.4, 200 mM Na tartrate, 0.1% Tween® 20, 0.2% bovine serum albumin.

Determination of the reactivity/cross-reaction with monomeric, human IgG1: In order to determine the reactivity/cross-reaction with monomeric, non-aggregated H-IgG1, the monoclonal antibody to be examined is pre-incubated in the test described above with monomeric, non-aggregated IgG1 in increasing concentrations or in excess. If the measured signal remains unchanged at a high level, there is no cross-reaction. If the measured signal decreases, a cross-reaction has occurred.

For this microtitre plates (MTP) (MicroCoat Company, Order No. 12-K 96 N) coated with recombinant streptavidin are coated with 1 μg/ml biotinylated H-IgG1 (=H-IgG1-Bi) in incubation buffer. 100 μl of the H-IgG1-Bi solution is used per well and incubated for 60 min at room temperature while shaking and subsequently washed 3 times with 0.9% NaCl/0.05% Tween® 20.

The monoclonal antibody to be tested for cross-reaction is pre-incubated with serial concentrations of up to 1 μg/ml monomeric, non-aggregated IgG1. The pre-incubation takes place in uncoated 96-well MTPs for 1 hour at room temperature while shaking.

In the next step 100 μl of this solution (antibody+non-aggregated, monomeric IgG1 in excess) is added to a coated well and incubated for 1 hour at room temperature while shaking. After washing 3 times with 0.9% sodium chloride/0.05% Tween® 20, 100 μl of a POD-labeled Fab fragment of a polyclonal antibody from the goat against mouse IgM (Dianova Company, Order No. 115-036-075, concentration used 0.16 μg/ml incubation buffer) is added in each case to detect bound antibody from the sample, incubated for 1 hour at room temperature while shaking and subsequently washed 3 times with 0.9% sodium chloride/0.05% Tween® 20.

Finally 100 μl/well ABTS® substrate (Roche Diagnostics GmbH, Order No. 1684 302) is added and the absorbance at 405/492 nm is measured after 30 min at room temperature in an MR700 Microplate reader from the Dynatech Company.

The monoclonal rheumatoid factor-like binding antibodies that are suitable in the sense of the disclosure recognize all human IgG subclasses and exhibit less than 10% cross-reaction with monomeric h-IgG in a competition test. If H-IgG1 polymer is used to determine the reactivity, the measured signal is greatly reduced. Table 1 shows the major properties of the monoclonal antibodies that were found.

Fermentation of Hybridoma Clones to Isolate Monoclonal Antibodies:

The hybridoma cells that are obtained are sown at a density of 1×105 cells per ml in RPMI 1640 medium containing 10% FCS and propagated for 7 days in a fermenter (Thermodux Company, Wertheim/_Main, model MCS-104XL, Order No. 144-050). Average concentrations of 100 μg monoclonal antibody per ml are reached in the culture supernatant.

Isolation of Monoclonal MAb <h-Agg.-IgG>M-3.022.5-IgM:

5 mg MAb <h-Agg.-IgG>M-3.022.5-IgM (DSM ACC2873) is adjusted to a total volume of 2 ml with 0.1 M sodium phosphate buffer, pH 8.6. 50 μl of a 1.11 mM solution of digoxigenin-3-O-methyl-carbonyl-e-aminocaproic acid-N-hydroxysuccinimide ester in dimethyl sulfoxide is added to this solution and subsequently stirred for 60 min at 25° C. The ratio of IgM to activated digoxigenin is 1:10. The IgM-digoxigenin that forms is dialysed against 20 mM potassium phosphate buffer/0.1 M NaCl/3% sucrose, pH 7.5. The dialysed IgM-Dig is stored in aliquots at −80° C.

Example 3

Fully Automated ELISA Assay on a Multi Parameter Biochip Platform

A multiparameter biochip platform is described in Hornauer, H. et al., BIOspectrum, Special Proteomics 10 (2004) 564-565 and Hornauer, H. et al., Laborwelt 4 (2004) 38-39.

A streptavidin coating is applied over the whole area of a test area of about 2.5×6 mm on a black-stained polystyrene support (solid phase). Lines of identical spots of approximately 10 to 20 per line consisting of biotinylated fragments of the therapeutic antibody are applied to the test area in an ink-jet procedure; the diameter per spot is about 150 μm.

The Following Test-Specific Reagents were Used:
Sample Dilution Buffer:
50 mM Tris, pH 7.6; 150 mM NaCl; 0.1% detergent (polydocanol); 0.6% BSA; 0.2% preservative (oxypyrion and methylisothiazolone hydrochloride (MIT))
Wash Buffer:
10 mM Tris, 0.01% polydocanol, 0.001% oxypyrion, 0.001% MIT
Samples:
human sera, positive samples were obtained by screening study populations which were treated with the respective therapeutic antibody; the negative samples are healthy blood donors not treated with the respective therapeutic antibody.

Infliximab Fab fragments were used as biotinylated antigens. Auto-antibodies (anti-<TmAB>AB) against these antigens were detected in an indirect test format. 50 μg/ml of the respective biotinylated antigen was used in each spot solution.

Description of the test procedure: The samples were diluted 1:50 with the sample dilution buffer for the measurement. The diluted samples were incubated for 12 min at 37° C. After aspirating the sample and washing the test field with wash buffer, they were incubated with the MAb <h-Agg.-IgG>M-3.022.5-IgM (DSM ACC2873), an antibody labeled with digoxin (Dig-labeled monoclonal antibody <h-Agg.-IgG>), for 6 min at 37° C. with a subsequent washing step. After incubation with a fluorescently labeled <Dig> antibody for 3 min at 37° C. and subsequently washing and suction drying the test field, the signals were detected by a CCD camera.

Example 4

Comparison of F(ab')$_2$ and Fab Fragments in an Indirect Assay Format

Biotinylated infliximab, as fragments F(ab')$_2$-Bi or Fab-Bi, is spotted each onto a distinct area on a chip surface (solid phase). Digoxigenated anti-<human IgG> is used as detection reagents. As infliximab is a humanized IgG1, the detection antibody would bind directly to the spotted antibody. Therefore only the use of infliximab fragments (in more general anti-<TNFα antibody fragments>) F(ab')$_2$-Bi or Fab-Bi is possible in this assay format.

Figure 5A:
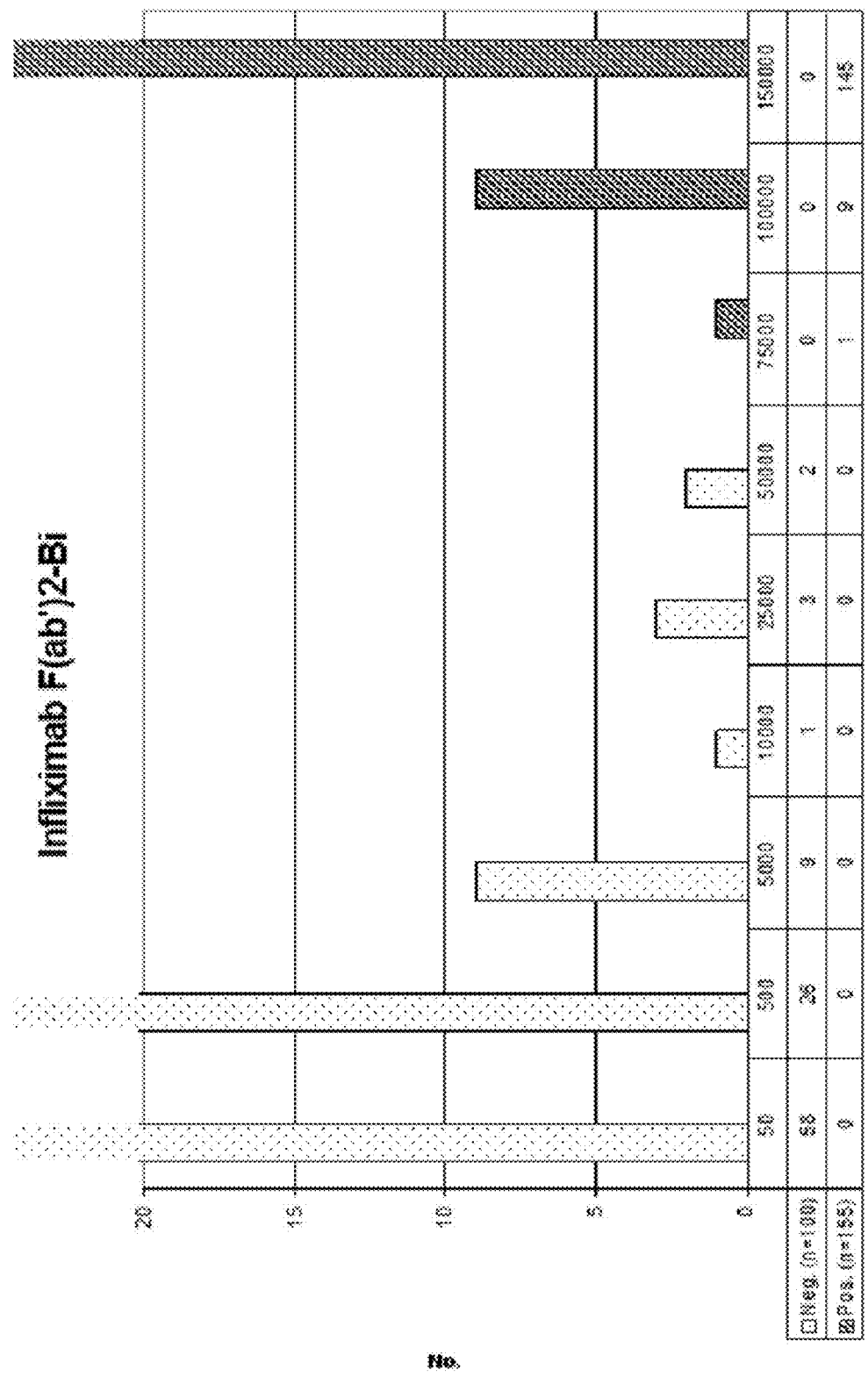
FIG. 5a is a bar graph showing the results of a comparison between serum samples taken from apparently healthy human blood donors (TN) and serum samples taken from RA patients treated with infliximab (TP), contacted with F(ab')$_2$-Bi infliximab fragments as capture antibody (columns of 50, 500, and 150000 are truncated in height).

In total 100 serum samples from apparently healthy blood donors (TN) as well as 155 serum samples from rheumatoid arthritis (RA) patients treated with infliximab (TP) were taken to compare the specificity of the two different assays, using infliximab fragments Fab-Bi or F(ab')$_2$-Bi as capture antibodies. The use of biotinylated infliximab as F(ab')$_2$-Bi results in falsely elevated signals in samples taken from several apparently healthy blood donors (TN) which were almost as strong as the signals of samples taken from truly positive (TP) rheumatoid arthritis patients treated with infliximab (Results are shown in Table 2 and a graphical representation of the results is given in FIG. 5a).

TABLE 2

Use of Biotinylated F(ab')$_2$-Bi Fragment of Infliximab as Capture Antibody
Infliximab fragment F(ab')$_2$-Bi

| Counts | 50 | 500 | 5000 | 10000 | 25000 | 50000 | 75000 | 100000 | 150000 |
|---|---|---|---|---|---|---|---|---|---|
| TN (n = 100) | 58 | 26 | 9 | 1 | 3 | 2 | 0 | 0 | 0 |
| TP (n = 155) | 0 | 0 | 0 | 0 | 0 | 6 | 1 | 9 | 145 |

Figure 5B:
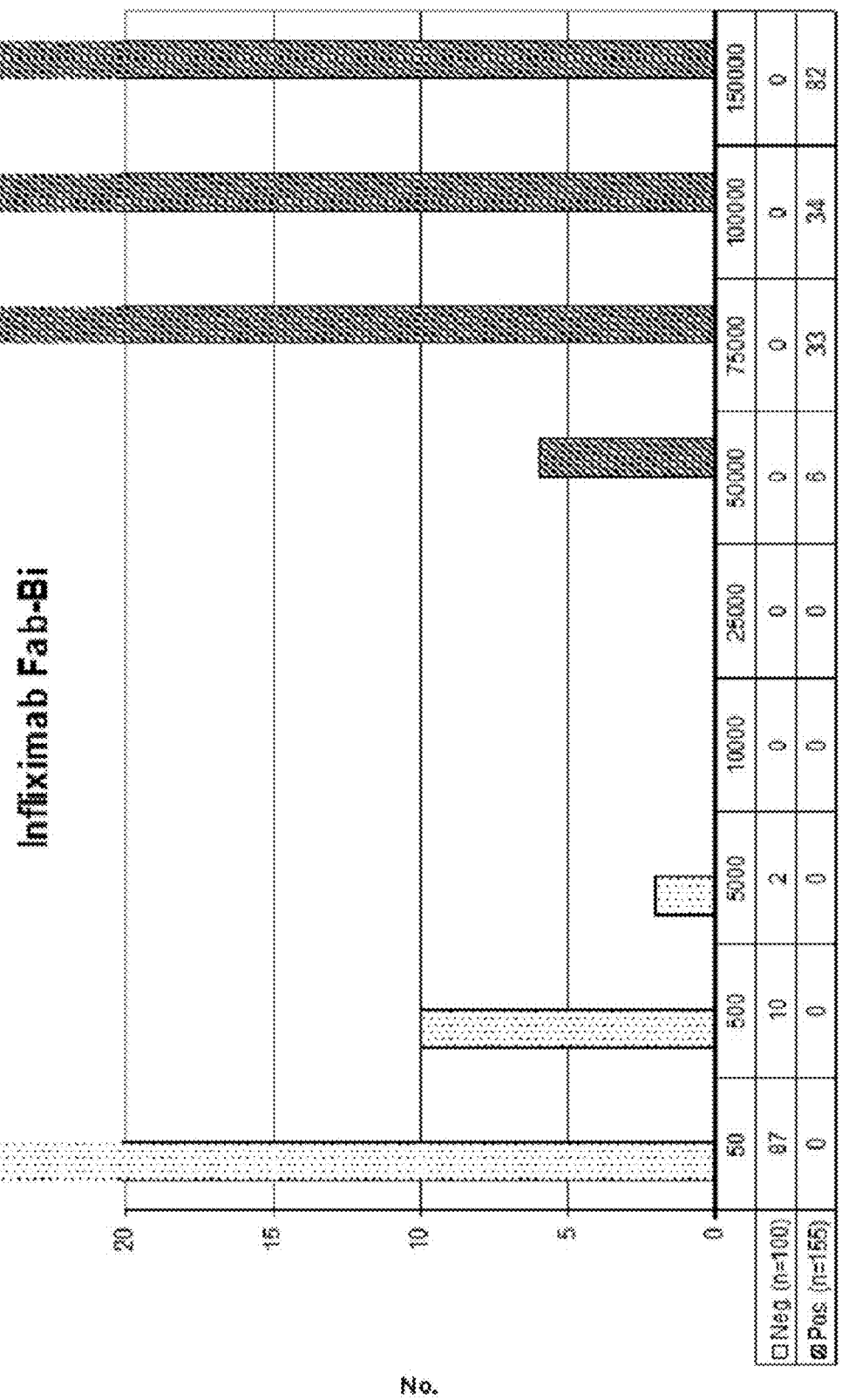
FIG. 5b is a bar graph showing the results of a comparison between serum samples taken from apparently healthy human blood donors (TN) and serum samples taken from RA patients treated with infliximab (TP), contacted with Fab-Bi infliximab fragments as capture antibody (columns of 50, 75000, 100000 and 150000 are truncated in height).

The use of biotinylated Fab-Bi fragment of infliximab as capture antibody allowed us for a much better differentiation between true positive (TP) and true negative (TN) samples. Results are shown in Table 3 and a graphical representation of the results is given in FIG. 5b.

TABLE 3

Use of Biotinylated Fab-Bi Fragment of Infliximab as Capture Antibody
Infliximab fragment Fab-Bi

| Counts | 50 | 500 | 5000 | 10000 | 25000 | 50000 | 75000 | 100000 | 150000 |
|---|---|---|---|---|---|---|---|---|---|
| TN (n = 100) | 87 | 10 | 2 | 0 | 0 | 0 | 0 | 0 | 0 |
| TP (n = 155) | 0 | 0 | 0 | 0 | 0 | 6 | 33 | 34 | 82 | tion reagents. As infliximab is a humanized IgG1, the detection antibody would bind directly to the spotted antibody. Therefore only the use of infliximab fragments (in more general anti-<TNFα antibody fragments>) F(ab')$_2$-Bi or Fab-Bi is possible in this assay format.

As shown by the results from Example 4, the use of Fab fragments is preferred. In the indirect assay format Fab fragments result in a much better differentiation between negative and truly positive results.

Example 5

Screening Assays for Detection of Anti-<TNFα Antibody> Antibodies (Anti-<TNFαAB>ABs)

Study data are based on samples from the Copenhagen Cohort. Blood samples were taken from a total of 218 patients with rheumatoid arthritis (RA) treated with infliximab. This blood samples were analyzed for the presence of anti-<TmAB>ABs to infliximab (anti-<TNFαAB>ABs). A baseline sample (reference sample) is taken at week 0, before first administration of a TmAB. If a sample is stated herein to be taken at week 2 after first administration of a TmAB, the sample can be taken from the 9$^{th}$ day to the 21$^{st}$ day. If a sample is stated herein to be taken at week 6 after first administration of a TmAB, the sample can be taken from the 28$^{th}$ day to the 64$^{th}$ day. If a sample is stated herein to be taken at week 14 after first administration of a TmAB, the sample can be taken from week 13 to week 16.

Anti-<TmAB>AB to infliximab are determined using an indirect assay format as described. A complete overview of rare reagents, buffers, calibrators and controls are given in Example 3.

Indirect Assay Format:

Biotinylated infliximab, as Fab-Bi, is spotted onto a chip surface. Digoxigenated anti-<human IgG> is used as detec-

TABLE 4

| | anti- < TmAB > AB indirect Assay (optimized for sensitivity) | | |
|---|---|---|---|
| Time point | week 2 | week 6 | week 14 |
| no of patients with anti- < TmAB > AB+ test result | 4 | 31 | 43 |
| no of patients withdrawn due to ADR before week 50 | 3 | 15 | 16 |
| Percentage withdrawn | 75% | 48% | 37% |
| no of patients with anti- < TmAB > AB− test result | | 94 | 88 |
| no of patients withdrawn due to ADR before week 50 | | 12 | 12 |
| Percentage withdrawn | | 13% | 14% |
| Hazard ratio (95% CI) | | 5.06 (2.36-10.84) | 3.30 (1.54-6.99) |
| p value | | <0.0001 | 0.0009 |

The anti-<TmAB>AB indirect assay format shown in FIG. 1 with a superior sensitivity detects anti-<TmAB>ABs in samples taken from patients as early as 2 weeks after first therapeutic administration of infliximab.

Later on withdrawal from the Study due to an ADR can be predicted by anti-<TmAB>AB determination:

Early development of anti-<TmAB>AB at week 2 or week 6 let us predict a later ADR and drop-out of the patients from the study with 75% and 48% probability, respectively (data shown in Table 4).

Treatment with a TmAB, e.g. infliximab lead to anti-<TmAB>AB formation against said TmAB in a minority but still significant number of patients. Most importantly a high number of these patients left the study due to ADRs at a later point in time. These findings might indicate that anti-drug antibodies—assessed in a method according to the present disclosure—can be detected before ADRs set in and thus it may be possible to use a positive test for anti-<TmABs> antibodies to better direct therapy, e.g. to switch from a first TmAB to a second, alternative TmAB All references cited in this specification are herewith incorporated by reference with respect to their entire disclosure content and the disclosure content specifically mentioned in this specification.

While this disclosure has been described as having an exemplary design, the present disclosure may be further modified within the spirit and scope of this disclosure. This application is therefore intended to cover any variations, uses, or adaptations of the disclosure using its general principles. Further, this application is intended to cover such departures from the present disclosure as come within the known or customary practice in the art to which this disclosure pertains.

What is claimed is:

1. A method for determination of an anti-<therapeutic monoclonal antibody> antibody (anti<TmAB>AB) in a whole blood, serum and plasma sample from a patient treated with a therapeutic monoclonal antibody (TmAB), the method comprising:
   a) providing a F(ab) fragment of the TmAB bound to a solid phase;
   b) incubating the solid phase provided in (a) with the sample, thereby binding the anti <TmAB>AB to the solid phase via the F(ab) fragment;
   c) incubating the solid phase obtained in (b) with a monoclonal antibody <h-Agg.-IgG>, whereby said monoclonal antibody binds to the anti<TmAB>AB, wherein said monoclonal antibody is an IgM antibody having a dissociation constant ($=K_D$) value of about $10^{-6}$ mol/l-$10^{-8}$ mol/l; and
   d) detecting the monoclonal antibody<h-Agg.-IgG> bound in (c) and thereby determining the anti<TmAB>AB in the sample.

2. The method according to claim 1, wherein the TmAB is selected from the group consisting of chimeric antibodies (CA) and humanized antibodies (HA).

3. The method according to claim 1, wherein the TmAB is selected from the group consisting of infliximab, adalimumab, certolizumab and rituximab.

4. The method according to claim 1, wherein the F(ab) fragment is bound to the solid phase by a binding system selected from the group consisting of biotin/steptavidin, biotin/avidin, and biotin/anti-<biotin> antibody.

5. The method according to claim 1, wherein the monoclonal antibody is an antibody having a dissociation constant ($K_D$) value of between approximately $10^{-7}$ mol/l-$10^{-8}$ mol/l.

6. The method according to claim 1, wherein the monoclonal antibody<h-Agg.-IgG> is labeled.

7. The method according to claim 6, wherein the monoclonal antibody<h-Agg.-IgG> is labeled with Dig.

8. The method according to claim 7, wherein the Dig-labeled monoclonal antibody <h-Agg.-IgG> is detected by incubating with an anti-<Dig> antibody conjugated to a detectable label.

9. The method according to claim 8, wherein the detectable label is selected from the group consisting of luminescent labels, chemiluminescent labels, electrochemiluminescent labels, fluorescent labels, and radioactive labels.

* * * * *